US007833969B2

(12) United States Patent
Dengjel

(10) Patent No.: US 7,833,969 B2
(45) Date of Patent: Nov. 16, 2010

(54) TUMOR-ASSOCIATED PEPTIDES BINDING PROMISCUOUSLY TO HUMAN LEUKOCYTE ANTIGEN (HLA) CLASS II MOLECULES

(75) Inventor: Jörn Dengjel, Odense (DK)

(73) Assignee: Immatics Biotechnologies GmbH, Tubingen (DE)

( * ) Notice: Subject to any disclaimer, the term of this patent is extended or adjusted under 35 U.S.C. 154(b) by 239 days.

(21) Appl. No.: 11/942,598

(22) Filed: Nov. 19, 2007

(65) Prior Publication Data
US 2008/0206217 A1 Aug. 28, 2008

Related U.S. Application Data

(62) Division of application No. 11/912,670, filed as application No. PCT/EP2006/008642 on Sep. 5, 2006.

(30) Foreign Application Priority Data
Sep. 5, 2005 (EP) ................................ 05019254

(51) Int. Cl.
*A61K 38/10* (2006.01)
(52) U.S. Cl. ..................... 514/2; 514/14; 424/93.71; 435/243
(58) Field of Classification Search ....................... None
See application file for complete search history.

(56) References Cited

U.S. PATENT DOCUMENTS

| 4,810,781 A | 3/1989 | Hollinshead |
| 6,312,937 B1 | 11/2001 | Ni et al. |
| 2003/0086934 A1 * | 5/2003 | Botstein et al. ........... 424/185.1 |

FOREIGN PATENT DOCUMENTS

| DE | 19936563 A1 | 8/2001 |
| WO | WO 0157275 | 9/2001 |
| WO | WO 0157276 | 9/2001 |
| WO | WO 02/50103 A2 | 6/2002 |
| WO | WO 02078516 | 10/2002 |
| WO | WO/02/094981 AS | 11/2002 |

OTHER PUBLICATIONS

Parker et al; Scheme for Ranking Potential . . . Peptide Side-Chains, Journal of Immunology; XP-00088437; 1994; pp. 163-175.
Park et al., Sequence of MET protooncogene cDNA . . . receptors; Proc. Natl. Acad. Sci. USA; XP-000941506; 1978; pp. 6379-6383.
Heid et al.; Adipocyte differentiation-related . . . membrane; Biochem J.; XP-002060680; 1996; pp. 1025-1030.
Database online; Human mRNA for KIAA0367 gene . . . ; XP-002353163; pp. 1-3.
Weinschenk et a l.; Integrated Functional . . . Antitumor Vaccines; Cancer Research, vol. 62; Oct. 15, 2002; pp. 5818-5827.
Schirle et al.; Identification of tumor-associated . . . approach; Eur. J. Immunol., vol. 30, XP-002246625; 2000; pp. 2216-2225.
Schmidt et al.; Induction of Adipophilin-Specific . . . Cell Lysis; Cancer Research, vol. 64, Feb. 1, 2004; pp. 1164-1170.
Kobayashi et al.; "Defining promiscous . . . Antigen," Cancer Research, Sep. 15, 2000, vol. 60, pp. 5228-5236.
Database Geneseq [online] Derwent; Jan. 23, 2003; XP002365849.
Database Geneseq [online] Derwent; Feb. 12, 2004; X002405482.
Database Geneseq [online] Derwent; Nov. 5, 2001; XP002365851.
Database Geneseq [online] Derwent; Nov. 6, 2001; XP002365850.
Database Geneseq [online] Derwent; Aug. 12, 2004; XP002425882.
Cheever et al., , "T-Cell Immunity to Oncogenic Proteins Including Mutated RAS and Chimeric BCR-ABLa", Annals N.Y. Acad. Sci. 1993 690:101-112.
Kobayashi et al., "Identification of an Antigenic Epitope for Helper T Lymphocytes From Carcinoembryonic Anigen", 2002, Clinical Cancer Research; 8:3219-3225.
Gnjatic et al., "Survey of Naturally Occurring CD4+ T-Cell Responses Against NY-ESO-1 Cancer Patiencs: Correlation With Antibody Responses", 2003, Proc. Natl. Acad. Sci. U.S.A. 100(15):8862-7.
Qin et al., "CD4+ T Cell-Mediated Tumor Rejection Involves Inhibition of Angiogenesis That Is Dependent on IFNY Receptor Expression by Nonhematopoietic Cells", Immunity vol. 12 677-686 Jun. 2000.
Kennedy et al., "CD4+ T Lymphocytes Play a Critical Role in Antibody Production and Tumor Immunity Against Simian Virus 40 Large Tumor Antigen". Cancer Research 63, 1040-1045, Mar. 1, 2003.
Mach et al., "Regulation of MHC Class II Genes: Lessons From a Disease" Annu. Rev. Immunol, 1996 14:301-31.
Chaux et al., "Identification of MAGE-3 Epitopes Presented by HLA-DR Molecules to CD4+ T Lymphocytes", J.Exp.Med. vol. 189, No. 5, Mar. 1, 1999 189:767-778.
Vigneron et al., "An Antigenic Peptide Produced by Peptide Splicing in the Proteasome", Science vol. 304, Apr. 23; 304 (5670):587-90.
Linehan et al., "Genetic Basis of Cancer of the Kidney: Disease-Specific Approaches to Therapy", American Association for Cancer Research, vol. 10, 6282s-6289s, Sep. 15, 2004.
McCarty et al., "Targeting P53 for Adoptive T-Cell Immunotherapy", Cancer Research 58 1998 15:58 2601-5.
Disis et al., "Immunity to the HER-2/NEU Oncogenic Protein", CIBA Found. Symp. 1994 187:198-211.
Marks et al., "A Lysosomal Targeting Signal in the Cytoplasmic Tail of the B Chain Directs HLA-DM to MHC Class II Compartments", 1995, J. Cell Biol. 131, 351-369.
Rodriguez et al., "DNA Immunization With Minigenes: Low Frequency of Memory Cytotoxic T Lymphocytes and Inefficinet Antiviral Protection are Rectified by Ubiquitination", 2001, Journal of Virology Jun. 1998, 5174-5181.

* cited by examiner

*Primary Examiner*—Christopher R. Tate
*Assistant Examiner*—Roy Teller
(74) *Attorney, Agent, or Firm*—Baker Donelson Bearman, Caldwell & Berkowitz, PC

(57) ABSTRACT

The present invention relates to immunotherapeutic methods, and molecules and cells for use in immunotherapeutic methods. In particular, the present invention relates to the immunotherapy of cancer. The present invention furthermore relates to tumor-associated T-helper cell peptide epitopes, alone or in combination with other tumor-associated peptides, that serve as active pharmaceutical ingredients of vaccine compositions which stimulate anti-tumor immune responses. In particular, the present invention relates to 49 novel peptide sequences derived from HLA class II molecules of human tumor cell lines which can be used in vaccine compositions for eliciting anti-tumor immune responses.

9 Claims, 6 Drawing Sheets

TUMOR-ASSOCIATED PEPTIDES BINDING PROMISCUOUSLY TO HUMAN LEUKOCYTE ANTIGEN (HLA) CLASS II MOLECULES

RELATED APPLICATIONS

This application is a divisional application of U.S. application Ser. No. 11/912,670, which was filed on Oct. 25, 2007, which is the National Phase application of PCT/EP2006/008642, filed Sep. 5, 2006, which claims priority to European Patent Application No. 05019254.1, filed Sep. 5, 2005, the entire contents of which are hereby incorporated.

The present invention relates to immunotherapeutic methods, and molecules and cells for use in immunotherapeutic methods. In particular, the present invention relates to the immunotherapy of cancer, in particular renal and colon cancer. The present invention furthermore relates to tumour-associated T-helper cell peptide epitopes, alone or in combination with other tumour-associated peptides, that serve as active pharmaceutical ingredients of vaccine compositions which stimulate anti-tumour immune responses. In particular, the present invention relates to 49 novel peptide sequences derived from HLA class II molecules of human tumour cell lines, which can be used in vaccine compositions for eliciting anti-tumour immune responses.

For the purposes of the present invention, all references as cited herein are incorporated by reference in their entireties.

BACKGROUND OF THE INVENTION

Stimulation of an immune response is dependent upon the presence of antigens recognised as foreign by the host immune system. The discovery of the existence of tumour associated antigens has now raised the possibility of using a host's immune system to intervene in tumour growth. Various mechanisms of harnessing both the humoral and cellular arms of the immune system are currently being explored for cancer immunotherapy.

Specific elements of the cellular immune response are capable of specifically recognising and destroying tumour cells. The isolation of cytotoxic T-cells (CTL) from tumour-infiltrating cell populations or from peripheral blood suggests that such cells play an important role in natural immune defences against cancer (Cheever et al., Annals N.Y. Acad. Sci. 1993 690:101-112). CD8-positive T-cells (TCD8$^+$) in particular, which recognise Class I molecules of the major histocompatibility complex (MHC)-bearing peptides of usually 8 to 10 residues derived from proteins located in the cytosol, play an important role in this response. The MHC-molecules in humans are also designated as human leukocyte-antigens (HLA).

There are two classes of MHC-molecules: MHC-I-molecules and MHC-molecules. MHC-I molecules can be found on most cells having a nucleus, and present peptides that result from proteolytic cleavage of endogenous proteins and larger peptides. MHC-II-molecules can be found only on professional antigen presenting cells (APC), and present peptides of exogenous proteins that are taken up by APCs during the course of endocytosis, and are subsequently processed. Complexes of peptide and MHC-I molecules are recognised by CD8-positive cytotoxic T-lymphocytes, and complexes of peptide and MHC-II molecules are recognised by CD4-positive-helper-T-cells.

CD4-positive helper T-cells play an important role in orchestrating the effector functions of anti-tumor T-cell responses and for this reason the identification of CD4-positive T-cell epitopes derived from tumor associated antigens (TAA) may be of great importance for the development of pharmaceutical products for triggering anti-tumor immune responses (Kobayashi, H., R. Omiya, M. Ruiz, E. Huarte, P. Sarobe, J. J. Lasarte, M. Herraiz, B. Sangro, J. Prieto, F. Borras-Cuesta, and E. Celis. 2002. Identification of an antigenic epitope for helper T lymphocytes from carcinoembryonic antigen. *Clin. Cancer Res.* 8:3219-3225., Gnjatic, S., D. Atanackovic, E. Jäger, M. Matsuo, A. Selvakumar, N. K. Altorki, R. G. Maki, B. Dupont, G. Ritter, Y. T. Chen, A. Knuth, and L. J. Old. 2003. Survey of naturally occurring CD4+ T-cell responses against NY-ESO-1 in cancer patients: Correlation with antibody responses. *Proc. Natl. Acad. Sci. U.S.A.* 100(15):8862-7).

It was shown in mammalian animal models, e.g., mice, that even in the absence of cytotoxic T lymphocyte (CTL) effector cells (i.e., CD8-positive T lymphocytes), CD4-positive T-cells are sufficient for inhibiting visualization of tumors via inhibition of angiogenesis by secretion of interferon-gamma (IFNγ) (Qin, Z. and T. Blankenstein. 2000. CD4+ T-cell-mediated tumor rejection involves inhibition of angiogenesis that is dependent on IFN gamma receptor expression by non-hematopoietic cells. *Immunity.* 12:677-686). Additionally, it was shown that CD4-positive T-cells recognizing peptides from tumor-associated antigens presented by HLA class II molecules can counteract tumor progression via the induction of an Antibody (Ab) responses (Kennedy, R. C., M. H. Shearer, A. M. Watts, and R. K. Bright. 2003. CD4$^+$ T lymphocytes play a critical role in antibody production and tumor immunity against simian virus 40 large tumor antigen. *Cancer Res.* 63:1040-1045). In contrast to tumor-associated peptides binding to HLA class I molecules, only a small number of class II ligands of TAA have been described so far (www.cancerimmunity.org, www.syfpeithi.de). Since the constitutive expression of HLA class II molecules is usually limited to cells of the immune system (Mach, B., V. Steimle, E. Martinez-Soria, and W. Reith. 1996. Regulation of MHC class II genes: lessons from a disease. *Annu. Rev. Immunol.* 14:301-331), the possibility of isolating class II peptides directly from primary tumors was not considered possible. Therefore, numerous strategies to target antigens into the class II processing pathway of antigen presenting cells (APCs) have been described. For example, the APCs having been incubated with the antigen of interest to enable it to be taken up, processed and presented (Chaux, P., V. Vantomme, V. Stroobant, K. Thielemans, J. Corthals, R. Luiten, A. M. Eggermont, T. Boon, and B. P. van der Bruggen. 1999. Identification of MAGE-3 epitopes presented by HLA-DR molecules to CD4(+) T lymphocytes. *J. Exp. Med.* 189:767-778), or cells have been transfected with genes or minigenes encoding the antigen of interest and fused to the invariant chain, which mediates the translocation of antigens to the lysosomal MHC class II processing and assembling compartment (MIIC).

For a peptide to trigger (elicit) a cellular immune response, it must bind to an MHC-molecule. This process is dependent on the allele of the MHC-molecule and specific polymorphisms of the amino acid sequence of the peptide. MHC-class-1-binding peptides are usually 8-10 residues in length and contain two conserved residues ("anchor") in their sequence that interact with the corresponding binding groove of the MHC-molecule.

In the absence of inflammation, expression of MHC class II molecules is mainly restricted to cells of the immune system, especially professional antigen-presenting cells (APC), e.g., monocytes, monocyte-derived cells, macrophages, dendritic cells.

The antigens that are recognised by the tumour specific cytotoxic T-lymphocytes, that is, their epitopes, can be molecules derived from all protein classes, such as enzymes, receptors, transcription factors, etc. Furthermore, tumour associated antigens, for example, can also be present in tumour cells only, for example as products of mutated genes or from alternative open reading frames (ORFs), or from protein splicing (Vigneron N, Stroobant V, Chapiro J, Ooms A, Degiovanni G, Morel S, van der Bruggen P, Boon T, Van den Eynde B J. An antigenic peptide produced by peptide splicing in the proteasome. Science. 2004 Apr. 23; 304 (5670):587-90.). Another important class of tumour associated antigens are tissue-specific structures, such as CT ("cancer testis")-antigens that are expressed in different kinds of tumours and in healthy tissue of the testis.

Various tumour associated antigens have been identified. Further, much research effort is being expended to identify additional tumour associated antigens. Some groups of tumour associated antigens, also referred to in the art as tumour specific antigens, are tissue specific. Examples include, but are not limited to, tyrosinase for melanoma, PSA and PSMA for prostate cancer and chromosomal cross-overs such as bcr/abl in lymphoma. However, many tumour associated antigens that have been identified occur in multiple tumour types, and some, such as oncogenic proteins and/or tumour suppressor genes (tumour suppressor genes are, for example reviewed for renal cancer in Linehan W M, Walther M M, Zbar B. The genetic basis of cancer of the kidney. J. Urol. 2003 December; 170(6 Pt 1):2163-72) which actually cause the transformation event, occur in nearly all tumour types. For example, normal cellular proteins that control cell growth and differentiation, such as p53 (which is an example for a tumour suppressor gene), ras, c-met, myc, pRB, VHL, and HER-2/neu, can accumulate mutations resulting in upregulation of expression of these gene products thereby making them oncogenic (McCartey et al. Cancer Research 1998 15:58 2601-5; Disis et al. Ciba Found. Symp. 1994 187:198-211). These mutant proteins can be the target of a tumour specific immune response in multiple types of cancer.

For the proteins to be recognised by the cytotoxic T-lymphocytes as tumour-specific antigen, and to be used in a therapy, particular prerequisites must be fulfilled. The antigen should be expressed mainly by tumour cells and not by normal healthy tissues or at the very least, expressed in rather small amounts in normal healthy tissue. It is furthermore desirable that the respective antigen is not only present in one type of tumour, but also in high concentrations (e.g. copy numbers per cell). The presence of epitopes in the amino acid sequence of the antigen is essential, since such peptide ("immunogenic peptide") that is derived from a tumour associated antigen should lead to an in vitro or in vivo T-cell-response.

Until now, numerous strategies to target antigens into the class II processing pathway have been described. It is possible to incubate antigen presenting cells (APCs) with the antigen of interest to be taken up and processed (Chaux, P., Vantomme, V., Stroobant, V., Thielemans, K., Corthals, J., Luiten, R., Eggermont, A. M., Boon, T. & van der, B. P. (1999) *J. Exp. Med.* 189, 767-778). Other strategies use fusion proteins that contain lysosomal target sequences. Expressed in APCs, such fusion proteins direct the antigens into the class II processing compartment (Marks, M. S., Roche, P. A., van Donselaar, E., Woodruff, L., Peters, P. J. & Bonifacino, J. S. (1995) *J. Cell Biol.* 131, 351-369, Rodriguez, F., Harkins, S., Redwine, J. M., de Pereda, J. M. & Whitton, J. L. (2001) *J. Virol.* 75, 10421-10430).

T-helper cells play an important role in orchestrating the effector function of CTLs in anti-tumour immunity. T-helper cell epitopes that trigger a T-helper cell response of the TH1 type support effector functions of CD8-positive Killer T-cells, which include cytotoxic functions directed against tumour cells displaying tumour-associated peptide/MHC complexes on their cell surfaces. In this way tumour-associated T-helper cell peptide epitopes, alone or in combination with other tumour-associated peptides, can serve as active pharmaceutical ingredients of vaccine compositions which stimulate anti-tumour immune responses.

The major task in the development of a tumour vaccine is therefore the identification and characterisation of novel tumour associated antigens and immunogenic T-helper epitopes derived therefrom, that can be recognised by CD4-positive CTLs. Therefore, there is a need to provide novel amino acid sequences for peptides that have the ability to bind to a molecule of the human major histocompatibility complex (MHC) class-II. The present invention fulfils this need.

SUMMARY OF THE INVENTION

According to the present invention, a tumour associated peptide that is selected from the group of peptides comprising at least one sequence according to any of SEQ ID NO: 1 to SEQ ID NO: 49 is provided, wherein the peptide has the ability to bind to a molecule of the human major histocompatibility complex (MHC) class-II, provided that the peptide is not the intact human tumour associated polypeptide.

In another embodiment, tumor associated peptides of the present invention consist essentially of an amino acid sequence according to any of SEQ ID NO: 1 to SEQ ID NO: 49. Preferably the tumor associated peptide exhibits an overall length of between 9 and 100, and more preferably between 9 and 30 amino acids.

More preferably, tumor associated peptides of the present invention consist of an amino acid sequence according to any of SEQ ID NO: 1 to SEQ ID NO: 49. Preferably, tumour associated peptides of the present invention have the ability to bind to a molecule of the human major histocompatibility complex (MHC) class-II, in particular to HLA-DRB1*0101.

In another embodiment, tumor associated peptides of the present invention have the ability to bind to at least one additional molecule of the human major histocompatibility complex (MHC) class-II.

Tumor associated peptides of the present invention may include non-peptide bonds.

In another embodiment, tumor associated peptides of the present invention may comprise a fusion protein comprising N-terminal amino acids of the HLA-DR antigen-associated invariant chain (Ii).

The present invention also provides a nucleic acid, encoding a tumor associated peptide of the invention. The nucleic acid may be DNA, cDNA, PNA, CNA, RNA or combinations thereof.

Another embodiment of the present invention provides expression vectors capable of expressing a nucleic acid encoding a tumor associated peptide of the invention.

The present invention further provides a host cell comprising a nucleic acid according r an expression vector of the invention. Preferably, the host cell is a recombinant RCC or Awells cell.

In another embodiment of the invention, there is provided a method of producing a tumor associated peptide of the invention by culturing a host cell described above and isolating the peptide from the host cell or its culture medium.

The present invention also provides a pharmaceutical composition comprising a tumor associated peptide, a nucleic acid or an expression vector as described above and a pharmaceutically acceptable carrier. The pharmaceutical composition may be in the form of a cancer vaccine, and may optionally comprise at least one suitable adjuvant. The present invention further provides use of tumor associated peptides, nucleic acids expression vectors of the invention in medicine.

Another embodiment of the present invention provides methods of killing target cells in a patient, which target cells aberrantly express a polypeptide comprising an amino acid sequence disclosed in SEQ ID NO:1-49. The methods comprise administering to the patient an effective amount of a tumor associated peptide, a nucleic acid, or an expression vector of the present invention, wherein the amount of the peptide, nucleic acid or expression vector is effective to provoke an anti-target cell immune response in the patient.

The present invention also provides for the use of a tumour associated peptide, a nucleic acid, or an expression vector of the invention in the manufacture of a medicament for killing target cells in a patient, which target cells aberrantly express a polypeptide comprising an amino acid sequence disclosed in SEQ ID NO:1-49.

The medicament may be used for inducing an immune response, in particular a cellular immune response, more particularly a T-cell mediated immune response against cells of solid tumors, which cells express a human class II MHC molecule on their surface and present a polypeptide comprising an amino acid sequence disclosed in SEQ ID NO:1-49.

The present invention further provides an in vitro method for producing activated cytotoxic T lymphocytes (CTL), the method comprising contacting in vitro CTL with antigen loaded human class II MHC molecules expressed on the surface of a suitable antigen-presenting cell for a period of time sufficient to activate said CTL in an antigen specific manner, wherein the antigen is a tumor associated peptide of the present invention. In certain embodiments the antigen is loaded onto class II MHC molecules expressed on the surface of a suitable antigen-presenting cell by contacting a sufficient amount of the antigen with an antigen-presenting cell. In certain embodiments the antigen-presenting cell comprises an expression vector of the present invention. In certain preferred embodiments, the class II MHC molecule is HLA-DRB1*0101.

Another embodiment of the present invention provides activated cytotoxic T lymphocytes (CTL), produced by the method described above and which selectively recognize a cell that aberrantly expresses a polypeptide comprising an amino acid sequence presented in SEQ ID NO:1-49.

The present invention also provides a T-cell receptor (TCR), which recognizes a cell that aberrantly expresses a polypeptide comprising an amino acid sequence given SEQ ID NO:1-49, the TCR being obtainable from the cytotoxic T lymphocyte (CTL) of described above, or a functionally equivalent molecule to the TCR. The present invention provides nucleic acids encoding T-cell receptors (TCR) of the present invention and also provides expression vectors capable of expressing T-cell receptors (TCR) of the present invention.

Another embodiment of the present invention provides a method of killing target cells in a patient, which target cells aberrantly express a polypeptide comprising an amino acid sequence presented in SEQ ID NO:1-49. The method comprises administering to the patient an effective number of cytotoxic T lymphocytes (CTL) of the present invention and as described above.

The present invention further provides a method of killing target cells in a patient, which target cells aberrantly express a polypeptide comprising an amino acid sequence as disclosed in SEQ ID NO:1-49. The method comprises the steps of: (1) obtaining cytotoxic T lymphocytes (CTL) from the patient; (2) introducing into the cells a nucleic acid encoding a T-cell receptor (TCR) of the present invention, or a functionally equivalent molecule; and (3) introducing the cells produced in step (2) into the patient.

In certain preferred embodiments, the target cells are cancer cells, in particular cells of solid tumor that express a human class II MHC molecule on their surface and present a polypeptide comprising an amino acid sequence as presented in SEQ ID NO:1-49.

Another embodiment of the present invention provides the use of cytotoxic T lymphocytes of the present invention in the manufacture of a medicament for killing target cells in a patient, which target cells aberrantly express a polypeptide comprising an amino acid sequence given in SEQ ID NO:1-49.

BRIEF DESCRIPTION OF THE FIGURES

FIG. 5a: fragments derived from fragmentation of naturally processed and presented HLA Class II ligand from MMP7 corresponding to the peptide sequence with SEQ ID NO: 1 (SQDDIKGIQKLYGKRS). Annotated fragments are depicted in Table 5. FIG. 5b: fragments derived from fragmentation of synthetic peptide having the peptide sequence of SEQ ID NO: 1. Fragmentations of both synthetic and naturally processed peptides yield equivalent fragmentation patterns and allow deduction and confirmation of the primary amino acid sequence of the previously uncharacterized peptide sequence (SEQ ID NO: 1) of this HLA class II ligand from human MMP7.

DETAILED DESCRIPTION OF THE INVENTION

Figure 1A:
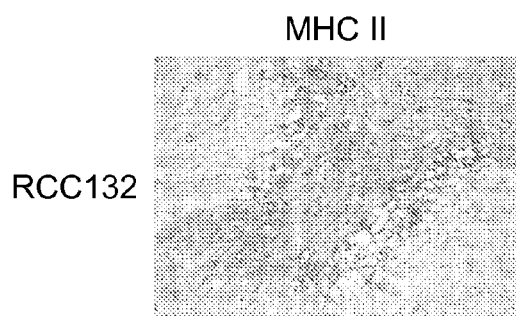
FIG. 1 shows the expression of HLA class II molecules in RCC of three patients. Whereas in the tumor of patient RCC132, the HLA positive cells were preferably localized at the margin (A,B) the HLA class II expression patterns of the tumors from patient RCC190 and RCC211 revealing a more papillary structure were more evenly spread (C,E,G). The visualization of CD68-positive macrophages (B,D,F) in serial tissue sections illustrates a close spatial relationship of tumor-infiltrating mononuclear immune cells and HLA II expressing tumor cells. Incubation with mouse IgG instead of specific antibodies consistently revealed negative staining results (H). Capital T marks the tumor.

In the present invention, the inventors demonstrate that it is possible to isolate and characterize peptides binding to HLA class II molecules directly from mammalian tumors, preferentially human tumors, preferentially solid tumors, e.g., from renal cell carcinomas and colon carcinomas. Infiltrating monocytes expressed MHC class II molecules as well as tumor cells, and, in addition, tumor cells showed up-regulation of several cytokine or chemokine-induced gene products, e.g., interferon gamma-induced gene products.

The present invention provides peptides stemming from antigens associated with tumorigenesis, and the ability to bind sufficiently to HLA class II molecules for triggering an immune response of human leukocytes, especially lymphocytes, especially T lymphocytes, especially CD4-positive T lymphocytes, especially CD4-positive T lymphocytes mediating $T_{H1}$-type immune responses. The peptides stem from tumor-associated antigens, especially tumor-associated antigens with functions in, e.g., proteolysis, angiogenesis, cell growth, cell cycle regulation, cell division, regulation of transcription, regulation of translation, tissue invasion, including, e.g., tumor-associated peptides from matrix-metalloproteinase 7 (MMP7; SEQ ID NO: 1) and insulin-like growth factor binding protein 3 (IGFBP3; SEQ ID NO: 25).

In the present invention the inventors also provide conclusive evidence that tumor-associated peptides sufficiently bind promiscuously to HLA-class II molecules, especially those HLA class II alleles genetically encoded by HLA DR loci of the human genome, are able to elicit immune responses mediated by human CD4-positive T-cells. CD4-positive T-cells were isolated from human peripheral blood, demonstrating that the claimed peptides are suitable for triggering T-cell responses of the human immune system against selected peptides of the tumor cell peptidome. As peptides can be synthesized chemically and can be used as active pharmaceutical ingredients of pharmaceutical preparations, the peptides provided by the inventors' invention can be used for immunotherapy, preferentially cancer immunotherapy.

To identify HLA class II ligands from TAA for the development of peptide-based immunotherapy, the inventors attempted to isolate HLA-DR-presented peptides directly from dissected solid tumors, in particular from renal cell carcinoma (RCC), which had been reported to be able to express class II molecules (Gastl, G., T. Ebert, C. L. Finstad, J. Sheinfeld, A. Gomahr, W. Aulitzky, and N. H. Bander. 1996. Major histocompatibility complex class I and class II expression in renal cell carcinoma and modulation by interferon gamma. *J. Urol.* 155:361-367). Even if the majority of tumor cells were class II negative, state-of-the-art mass spectrometers should provide the sensitivity required for identification of class II peptides from minimal numbers of tumor cells, or from infiltrating leukocytes which might cross-present TAA, or from stromal cells in the perimeter of the growing tumor.

The reasons for focusing on RCC to demonstrate technical proof of concept were the following: Around 150,000 people worldwide are newly diagnosed with RCC each year, the disease is associated with a high mortality rate, which results in approximately 78,000 deaths per annum (Pavlovich, C. P. and L. S. Schmidt. 2004. Searching for the hereditary causes of renal-cell carcinoma. *Nat. Rev. Cancer* 4:381-393). If metastases are diagnosed, the one-year survival rate decreases to approximately 60% (Jemal, A., R. C. Tiwari, T. Murray, A. Ghafoor, A. Samuels, E. Ward, E. J. Feuer, and M. J. Thun. 2004. Cancer statistics, 2004. *CA Cancer J. Clin.* 54:8-29), underlining the high unmet medical need in this indication. Because RCC seems to be an immunogenic tumor (Oliver R T D, Mehta A, Barnett M J. A phase 2 study of surveillance in patients with metastatic renal cell carcinoma and assessment of response of such patients to therapy on progression. Mol. Biother. 1988; 1:14-20. Gleave M, Elhilali M, Frodet Y, et al. Interferon gamma-1b compared with placebo in metastatic renal cell carcinoma. N Engl J. Med. 1998; 338:1265), as indicated by the existence of tumor-reacting and tumor-infiltrating CTL (Finke, J. H., P. Rayman, J. Alexander, M. Edinger, R. R. Tubbs, R. Connelly, E. Pontes, and R. Bukowski. 1990. Characterization of the cytolytic activity of CD4-positive and CD8-positive tumor-infiltrating lymphocytes in human renal cell carcinoma. *Cancer Res.* 50:2363-2370), clinical trials have been initiated to develop peptide-based anti-tumor vaccinations (Wierecky J, Mueller M, Brossart P. Dendritic cell-based cancer immunotherapy targeting MUC-1. Cancer Immunol Immunother. 2005 Apr. 28). However, due to the lack of helper T-cell epitopes from TAA, molecularly defined vaccines usually comprise peptides functioning as class I ligands only.

In the scientific work leading to the present invention, the inventors were able to isolate class II ligands from ten RCC samples, three colorectal carcinomas (CCA) and one transitional cell carcinoma (TCC, urothelial carcinoma). Only selected of the ligands from TAA identified by this approach have the unifying capacity to 1. Stem from antigens with known tumor association;
2. Bind to the most common HLA class II DR allele, HLA DRB1*0101; and
3. Have characteristics setting them apart from the majority of HLA class II ligands, in that they fulfill criteria regarding their primary amino acid sequence allowing them to promiscuously bind to HLA-DR molecules from at least two different alleles.

As exemplified below with a peptide from MMP7 (SEQ ID NO: 1), these promiscuously HLA-DR-binding, tumor-associated peptides were found to be recognized by CD4-positive T-cells.

A first aspect of the invention provides a peptide, comprising an amino acid sequence according to any of SEQ ID NO: 1 to SEQ ID NO: 49 or a variant thereof provided that the peptide is not the intact human polypeptide from which the amino acid sequence is derived (i.e. one of the full-length sequences as listed in the locus link IDs (Accession numbers, see the attached Table 1, below).

As described herein below, the peptides that form the basis of the present invention have all been identified as being presented by MHC class II bearing cells (RCC). Thus, these particular peptides as well as other peptides containing the sequence (i.e. derived peptides) will most likely all elicit a specific T-cell response, although the extent to which such response will be induced might vary from individual peptide to peptide. Differences, for example, could be caused due to mutations in said peptides (see below). The person of skill in the present art is well aware of methods that can be applied in order to determine the extent to which a response is induced by an individual peptide, in particular with reference to the examples herein and the respective literature.

Preferably, a peptide according to the present invention consists essentially of an amino acid sequence according to any of SEQ ID NO: 1 to SEQ ID NO: 49 or a variant thereof.

"Consisting essentially of" shall mean that a peptide according to the present invention, in addition to the sequence according to any of SEQ ID NO: 1 to SEQ ID NO: 49 or a variant thereof, contains additional N- and/or C-terminally located stretches of amino acids that are not necessarily forming part of the peptide that functions as core sequence of the peptide comprising the binding motif and as an immunogenic T-helper epitope.

Nevertheless, these stretches can be important in order to provide for an efficient introduction of the peptide according to the present invention into the cells. In one embodiment of the present invention, the peptide of the present invention comprises the 80 N-terminal amino acids of the HLA-DR antigen-associated invariant chain (p33, in the following "Ii") as derived from the NCBI, GenBank Accession-number X00497 (Strubin, M., Mach, B. and Long, E. O. The complete sequence of the mRNA for the HLA-DR-associated invariant chain reveals a polypeptide with an unusual transmembrane polarity EMBO J. 3 (4), 869-872 (1984)).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence. For example, a peptide may be modified so that it at least maintains, if not improves, the ability to interact with and bind a suitable MHC molecule, such as HLA-A, and so that it at least maintains, if not improves, the ability to generate activated CTL which can recognize and kill cells which express a polypeptide which contains an amino acid sequence as defined in the aspects of the invention. As can derived from the database as described in the following, certain positions of HLA-A binding peptides are typically anchor residues forming a core sequence fitting to the binding motif of the HLA binding groove.

Those amino acid residues that are not essential to interact with the T cell receptor can be modified by replacement with another amino acid whose incorporation does not substantially effect T cell reactivity and does not eliminate binding to the relevant MHC. Thus, apart from the proviso given, the peptide of the invention may be any peptide (by which term the inventors include oligopeptide or polypeptide) which includes the amino acid sequences or a portion or variant thereof as given.

It is furthermore known for MHC-class II presented peptides that these peptides are composed of a "core sequence" having a certain HLA-specific amino acid motif and, optionally, N- and/or C-terminal extensions that do not interfere with the function of the core sequence (i.e. are deemed as irrelevant for the interaction of the peptide and the T-cell). The N- and/or C-terminal extensions can be between 1 to 10 amino acids in length, respectively. Thus, a preferred peptide of the present invention exhibits an overall length of between 9 and 100, preferably between 9 and 30 amino acids. These peptide can be used either directly in order to load MHC class II molecules or the sequence can be cloned into the vectors according to the description herein below. As these peptides form the final product of the processing of larger peptides within the cell, longer peptides can be used as well. The peptides of the invention may be of any size, but typically they may be less than 100,000 in molecular weight, preferably less than 50,000, more preferably less than 10,000 and typically about 5,000. In terms of the number of amino acid residues, the peptides of the invention may have fewer than 1000 residues, preferably fewer than 500 residues, more preferably fewer than 100 residues.

If a peptide that is greater than around 12 amino acid residues is used directly to bind to a MHC molecule, it is preferred that the residues that flank the core HLA binding region are ones that do not substantially affect the ability of the peptide to bind specifically to the binding groove of the MHC molecule or to present the peptide to the CTL. However, as already indicated above, it will be appreciated that larger peptides may be used, especially when encoded by a polynucleotide, since these larger peptides may be fragmented by suitable antigen-presenting cells.

Examples for peptides of MHC ligands, motifs, variants, as well as certain examples for N- and/or C-terminal extensions can be, for example, derived from the database SYFPEITHI (Rammensee H, Bachmann J, Emmerich N P, Bachor O A, Stevanovic S. SYFPEITHI: database for MHC ligands and peptide motifs. Immunogenetics. 1999 November; 50(3-4): 213-9 at http://syfpeithi.bmi-heidelberg.com/ and the references as cited therein.

As non-limiting examples, certain peptides for HLA-DR in the database are K H K V Y A C E V T H Q G L S S derived from Ig kappa chain 188-203 (Kovats et al. Eur J. Immunol. 1997 April; 27(4):1014-21); K V Q W K V D N A L Q S G N S derived from Ig kappa chain 145-159 (Kovats et al. Eur J. Immunol. 1997 April; 27(4):1014-21), L P R L I A F T S E H S H F derived from GAD65 270-283 (Endl et al. J Clin Invest. 1997 May 15; 99(10):2405-15) or F F R M V I S N P A A T H Q D I D F L I derived from GAD65 556-575 (Endl et al. J Clin Invest. 1997 May 15; 99(10):2405-15). In addition, peptides can also be derived from mutated sequences of antigens, such as in the case of A T G F K Q S S K A L Q R P V A S derived from bcr-abl 210 kD fusion protein (ten Bosch et al. Blood. 1996 Nov. 1; 88(9):3522-7), G Y K V L V L N P S V A A T derived from HCV-1 NS3 28-41 Diepolder et al. J. Virol. 1997 August; 71(8):6011-9), or F R K Q N P D I V I Q Y M D D L Y V G derived from HIV-1 (HXB2) RT 326-345 (van der Burg et al. J. Immunol. 1999 Jan. 1; 162(1):152-60). All "anchor" amino acids (see Friede et al., Biochim Biophys Acta. 1996 Jun. 7; 1316(2):85-101; Sette et al. J. Immunol. 1993 Sep. 15; 151(6):3163-70.; Hammer et al. Cell. 1993 Jul. 16; 74(1):197-203., and Hammer et al. J Exp Med. 1995 May 1; 181(5):1847-55. As examples for HLA-DR4) have been indicated in bold, the putative core sequences have been underlined.

All the above described peptides are encompassed by the term "variants" of the given amino acid sequence.

By "peptide" the inventors include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Typically, the peptide of the invention is one which, if expressed in an antigen presenting cell, may be processed so that a fragment is produced which is able to bind to an appropriate MHC molecule and may be presented by a suitable cell and elicit a suitable T-cell response. It will be appreciated that a fragment produced from the peptide may also be a peptide of the invention. Conveniently, the peptide of the invention contains a portion that includes the given amino acid sequence or a portion or variant thereof and a further portion which confers some desirable property. For example, the further portion may include a further T-cell epitope (whether or not derived from the same polypeptide as the first T-cell epitope-containing portion) or it may include a carrier protein or peptide. Thus, in one embodiment the peptide of the invention is a truncated human protein or a fusion protein of a protein fragment and another polypeptide portion provided that the human portion includes one or more inventive amino acid sequences.

In a particularly preferred embodiment, the peptide of the invention includes the amino acid sequence of the invention and at least one further T-cell epitope wherein the further T-cell epitope is able to facilitate the production of a T-cell response directed at the type of tumour that aberrantly expresses a tumour-associated antigen. Thus, the peptides of the invention include so-called "beads on a string" polypeptides which can also be used as vaccines.

It will be appreciated from the following that in some applications the peptides of the invention may be used directly (i.e. they are not produced by expression of a polynucleotide in a patient's cell or in a cell given to a patient); in such applications it is preferred that the peptide has fewer than 100 or 50 residues. A preferred peptide of the present invention exhibits an overall length of between 9 and 30 amino acids.

Preferably, the peptides of the invention are able to bind to HLA-DR. More preferably, the peptides bind selectively to HLA-DRB1*0101.

In another aspect of the present invention, similar to the situation as explained above for MHC class II molecules, the peptides of the invention may be used to trigger an MHC class I specific T cell response. A preferred MHC class I specific peptide of the present invention exhibits an overall length of between 9 and 16, preferably between 9 and 12 amino acids. It shall be understood that those peptides might be used (for example in a vaccine) as longer peptides, similar to MHC class II peptides. Methods to identify MHC class I specific "Core sequences" having a certain HLA-specific amino acid motif for HLA class I-molecules are known to the person of skill and can be predicted, for example, by the computer programs PAProC and SYFPEITHI.

The peptides of the invention are particularly useful in immunotherapeutic methods to target and kill cells that aberrantly express polypeptides that form the basis for the present peptides of the invention. Since these specific peptides consisting of the given amino acid sequences bind to HLA-DR it is preferred that the peptides of the invention are ones that bind HLA-DR and when so bound, the HLA-DR-peptide complex when present on the surface of a suitable antigen-presenting cell, is capable of eliciting the production of a CTL that recognises a cell that aberrantly expresses a polypeptide comprising the given amino acid sequence.

In one embodiment of the present invention, the peptide of the present invention comprises the 80 N-terminal amino acids of the HLA-DR antigen-associated invariant chain (p33, in the following "Ii") as derived from the NCBI, GenBank Accession-number X00497 (see also below).

By "aberrantly expressed" we include the meaning that the polypeptide is over-expressed compared to normal levels of expression or that the gene is silent in the tissue from which the tumour is derived but in the tumour it is expressed. By "over-expressed" we mean that the polypeptide is present at a level at least 1.2× that present in normal tissue; preferably at least 2× and more preferably at least 5× or 10× the level present in normal tissue.

Peptides (at least those containing peptide linkages between amino acid residues) may be synthesised by the Fmoc-polyamide mode of solid-phase peptide synthesis as disclosed by Lu et al (1981) J. Org. Chem. 46,3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethandithiol, phenol, anisole and water, the exact choice depending on the constituent amino acids of the peptide being synthesized. Also a combination of solid phase and solution phase methodologies for the synthesis of peptides is possible (see, for example, Bruckdorfer T, Marder O. Albericio F. From production of peptides in milligram amounts for research to multi-tons quantities for drugs of the future. Curr Pharm Biotechnol. 2004 February; 5(1):29-43 and the references as cited therein).

Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK.

Purification may be effected by any one, or a combination of, techniques such as size exclusion chromatography, ion-exchange chromatography, hydrophobic interaction chromatography and (usually) reverse-phase high performance liquid chromatography using acetonitril/water gradient separation.

Analysis of peptides may be carried out using thin layer chromatography, reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (e.g. polynucleotide) encoding a peptide of the invention. The polynucleotide may be DNA, cDNA, PNA, CNA, RNA or combinations thereof and it may or may not contain introns so long as it codes for the peptide. Of course, it is only peptides that contain naturally occurring amino acid residues joined by naturally occurring peptide bonds that are encodable by a polynucleotide. A still further aspect of the invention provides an expression vector capable of expressing a polypeptide according to the invention.

A variety of methods have been developed to operably link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or E. coli DNA polymerase I, enzymes that remove protruding, 3'-single-stranded termini with their 3'-5'-exonucleolytic activities, and fill in recessed 3'-ends with their polymerising activities.

The combination of these activities therefore generates blunt-ended DNA segments. The blunt-ended segments are then incubated with a large molar excess of linker molecules in the presence of an enzyme that is able to catalyse the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) Science 239, 487-491. This method may be used for introducing the DNA into a suitable vector, for example by engineering in suitable restriction sites, or it may be used to modify the DNA in other useful ways as is known in the art. In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued 3 Apr. 1984 to Rutter et al.; U.S. Pat. No. 4,530,901 issued 23 Jul. 1985 to Weissman; U.S. Pat. No. 4,582,800 issued 15 Apr. 1986 to Crowl; U.S. Pat. No. 4,677,063 issued 30 Jun. 1987 to Mark et al.; U.S. Pat. No. 4,678,751 issued 7 Jul. 1987 to Goeddel; U.S. Pat. No. 4,704,362 issued 3 Nov. 1987 to Itakura et al.; U.S. Pat. No. 4,710,463 issued 1 Dec. 1987 to Murray; U.S. Pat. No. 4,757,006 issued 12 Jul. 1988 to Toole, Jr. et al.; U.S. Pat. No. 4,766,075 issued 23 Aug. 1988 to Goeddel et al.; and U.S. Pat. No. 4,810,648 issued 7 Mar. 1989 to Stalker, all of which are incorporated herein by reference.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells. Preferably, the system can be RCC or Awells cells.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention. Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells. An example of an inducible mammalian expression vector is pMSG, also available from Pharmacia. This vector uses the glucocorticoid-inducible promoter of the mouse mammary tumour virus long terminal repeat to drive expression of the cloned gene. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). Other vectors and expression systems are well known in the art for use with a variety of host cells.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al. (1972) Proc. Natl. Acad. Sci. USA 69,2110 and Sambrook et al. (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs (1978) Nature 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) J. Mol. Biol. 98,503 or Berent et al.; (1985) Biotech. 3,208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies. Thus, in addition to the transformed host cells themselves, the present invention also contemplates a culture of those cells, preferably a monoclonal (clonally homogeneous) culture, or a culture derived from a monoclonal culture, in a nutrient medium.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules.

A further aspect of the invention provides a method of producing a peptide for intravenous (i.v.) injection, sub-cutaneous (s.c.) injection, intradermal (i.d.) injection, intraperitoneal (i.p.) injection, intramuscular (i.m.) injection. Preferred methods of peptide injection are s.c., i.d., i.p., i.m., and i.v. Preferred ways of DNA injection are i.d., i.m., s.c., i.p. and i.v. Doses of between 1 and 500 mg of peptide or DNA may be given.

A further aspect of the invention relates to the use of a tumour associated peptide according to the invention, a nucleic acid according to the invention or an expression vector according to the invention in medicine.

A further aspect of the invention provides a method of killing target cells in a patient which target cells aberrantly express a polypeptide comprising an amino acid sequence of the invention, the method comprising administering to the patient an effective amount of a peptide according to the invention, or an effective amount of a polynucleotide or an expression vector encoding a said peptide, wherein the amount of said peptide or amount of said polynucleotide or expression vector is effective to provoke an anti-target cell immune response in said patient. The target cell is typically a tumour or cancer cell.

The peptide or peptide-encoding nucleic acid constitutes a tumour or cancer vaccine. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant such as Detox, or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker et al (1993) Ann. NY Acad. Sci. 690, 276-291). The peptide may also be tagged, or be a fusion protein, or be a hybrid molecule. The peptides whose sequence is given in the present invention are expected to stimulate CD4 CTL. However, stimulation is more efficient in the presence of help provided by CD4-positive T-cells. Thus, the fusion partner or sections of a hybrid molecule suitably provide epitopes which stimulate CD4-positive T-cells. CD4-positive stimulating epitopes are well known in the art and include those identified in tetanus toxoid. The polynucleotide may be substantially pure, or contained in a suitable vector or delivery system.

Suitable vectors and delivery systems include viral, such as systems based on adenovirus, vaccinia virus, retroviruses, herpes virus, adeno-associated virus or hybrids containing elements of more than one virus. Non-viral delivery systems include cationic lipids and cationic polymers as are well known in the art of DNA delivery. Physical delivery, such as via a "gene-gun" may also be used. The peptide or peptide encoded by the nucleic acid may be a fusion protein, for example with an epitope which stimulates CD4-positive T-cells.

The peptide for use in a cancer vaccine may be any suitable peptide. In particular, it may be a suitable 9-mer peptide or a suitable 7-mer or 8-mer or 10-mer or 11-mer peptide or 12-mer. Longer peptides may also be suitable, but 9-mer or 10-mer peptides as described in the attached Table 1 are preferred.

Suitably, any nucleic acid administered to the patient is sterile and pyrogen free. Naked DNA may be given intramuscularly or intradermally or subcutaneously. The peptides may be given intramuscularly, intradermally, intraperitoneally, intravenously or subcutaneously (see also above regarding the method of producing a peptide). Preferably, the peptides as active pharmaceutical components are given in combination with an adjuvant, such as, for example, IL-2, IL-12, GM-CSF, incomplete Freund's adjuvant, complete Freund's adjuvant or liposomal formulations. The most preferred adjuvants can be found in, for example, Brinkman J A, Fausch S C, Weber J S, Kast W M. Peptide-based vaccines for cancer immunotherapy. Expert Opin Biol Ther. 2004 February; 4(2): 181-98.

Vaccination results in CTL responses stimulated by professional antigen presenting cells; once CTL are primed, there may be an advantage in enhancing MHC expression in tumor cells.

It may also be useful to target the vaccine to specific cell populations, for example antigen presenting cells, either by the site of injection, use of targeting vectors and delivery systems, or selective purification of such a cell population from the patient and ex vivo administration of the peptide or nucleic acid (for example dendritic cells may be sorted as described in Zhou et al. (1995) Blood 86, 3295-3301; Roth et al. (1996) Scand. J. Immunology 43, 646-651). For example, targeting vectors may comprise a tissue- or tumour-specific promoter which directs expression of the antigen at a suitable place.

A further aspect of the invention therefore provides a vaccine effective against cancer, or cancer or tumour cells, comprising an effective amount of a peptide according to the invention, or comprising a nucleic acid encoding such a peptide. It is also preferred that the vaccine is a nucleic acid vaccine. It is known that inoculation with a nucleic acid vaccine, such as a DNA vaccine, encoding a polypeptide leads to a T cell response. Most preferred is a vaccine comprising a (synthetic) peptide or peptides (i.e. either alone or in combinations of 1, 2, 3, 4, 5 or 6, 11 or even more peptides, see also further below).

Conveniently, the nucleic acid vaccine may comprise any suitable nucleic acid delivery means. The nucleic acid, preferably DNA, may be naked (i.e. with substantially no other components to be administered) or it may be delivered in a liposome or as part of a viral vector delivery system.

It is believed that uptake of the nucleic acid and expression of the encoded polypeptide by dendritic cells may be the mechanism of priming of the immune response; however, dendritic cells may not be transfected but are still important since they may pick up expressed peptide from transfected cells in the tissue.

Preferably the vaccine, such as DNA vaccine, is administered into the muscle or into the skin. The nucleic acid vaccine may be administered without adjuvant. The nucleic acid vaccine may also be administered with an adjuvant such as BCG or alum. Other suitable adjuvants include Aquila's QS21 stimulon (Aquila Biotech, Worcester, Mass., USA), which is derived from saponin, mycobacterial extracts and synthetic bacterial cell wall mimics, and proprietary adjuvants such as Ribi's Detox. Quil A, another saponin derived adjuvant, may also be used (Superfos, Denmark). Other adjuvants such as Freund's may also be useful. The nucleic acid vaccine is administered without adjuvant. It may also be useful to give the peptide conjugated to keyhole limpet haemocyanin, preferably also with an adjuvant.

Polynucleotide-mediated immunisation therapy of cancer is described in Conry et al. (1996) Seminars in Oncology 23, 135-147; Condon et al (1996) Nature Medicine 2, 1122-1127; Gong et al. (1997) Nature Medicine 3, 558-561; Zhai et al. (1996) J. Immunol. 156, 700-710; Graham et al. (1996) Int J. Cancer 65, 664-670; and Burchell et al. (1996) pp 309-313 In: Breast Cancer, Advances in biology and therapeutics, Calvo et al. (eds), John Libbey Eurotext, all of which are incorporated herein by reference in their entireties.

A still further aspect of the present invention provides the use of a peptide according to the invention, or of a polynucleotide or expression vector encoding such a peptide, in the manufacture of a medicament for killing target cells in a patient that target cells aberrantly express a polypeptide comprising an amino acid sequence of the invention.

A still further aspect of the present invention provides the use of a peptide according to the invention, or of a polynucleotide or expression vector encoding such a peptide, for the manufacture of a medicament for inducing an immune response, in particular a cellular immune response, more particularly a T-cell mediated immune response against cells of solid tumours which cells express a human class II MHC molecule on their surface and present a polypeptide comprising an amino acid sequence of the invention. It has been surprisingly found in the context of the present invention that tumour cells of solid tumours, in contrast to healthy cells of the same tissue, express human HLA class II molecule on their surface.

A further aspect of the invention thus provides a method for producing activated cytotoxic T lymphocytes (CTL) in vivo or in vitro, the method comprising contacting in vitro CTL with antigen-loaded human class II MHC molecules expressed on the surface of a suitable antigen-presenting cell for a period of time sufficient to activate, in an antigen specific manner, said CTL wherein the antigen is a peptide according to the invention.

Suitably, the CTL are CD4-positive helper cells, preferably of TH1-type. The MHC class II molecules may be expressed on the surface of any suitable cell and it is preferred if the cell is one which does not naturally express MHC class II molecules (in which case the cell is transfected to express such a molecule) or, if it does, it is defective in the antigen-processing or antigen-presenting pathways. In this way, it is possible for the cell expressing the MHC class II molecule to be primed substantially completely with a chosen peptide antigen before activating the CTL.

The antigen-presenting cell (or stimulator cell) typically has an MHC class II molecule on its surface and preferably is substantially incapable of itself loading said MHC class II molecule with the selected antigen. As is described in more detail below, the MHC class II molecule may readily be loaded with the selected antigen in vitro.

Preferably the mammalian cell lacks or has a reduced level or has reduced function of the TAP peptide transporter. Suitable cells that lack the TAP peptide transporter include T2, RMA-S and *Drosophila* cells. TAP is the Transporter Associated with antigen Processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Karre and Ljunggren (1985) J. Exp. Med. 162,1745.

It is preferable that the host cell expresses substantially no MHC class I molecules before transfection. Preferably, the stimulator cell expresses a molecule important for T-cell costimulation, such as any of B7.1, B7.2, ICAM-1 and LFA 3.

The nucleic acid sequences of numerous MHC class II molecules, and of the costimulator molecules, are publicly available from the GenBank and EMBL databases.

In a further embodiment, combinations of HLA molecules may also be used, such as, for example, MHC-class II molecules as described in the Tables A and B herein. The use of recombinant polyepitope vaccines for the delivery of multiple $CD8^+$ CTL epitopes is described in Thomson et al. (1996) J. Immunol. 157, 822-826 and WO 96/03144, both of which are incorporated herein by reference. In relation to the present invention, it may be desirable to include in a single vaccine, a peptide (or a nucleic acid encoding a peptide) wherein the peptide includes, in any order, an amino acid sequence of the present invention and another $CD8^+$ T cell-stimulating epitope. Such a vaccine would be particularly useful for treating cancers. Such "bead-on-a-string" vaccines are typically DNA vaccines. The simultaneous triggering of an MHC class II-dependent immune response together with an MHC class I-dependent immune response has the advantage that this leads to a local $TH_1$-like T-cell-reaction of CD4-positive T-cells, whereby the MHC class I-dependent CD8-positive T-cells are supported.

A number of other methods may be used for generating CTL in vitro. For example, the methods described in Peoples et al. (1995) Proc. Natl. Acad. Sci. USA 92, 432-436 and Kawakami et al. (1992) J. Immunol. 148,638643 use autologous tumor-infiltrating lymphocytes in the generation of CTL. Plebanski et al. (1995) Eur. J. Immunol. 25, 1783-1787 makes use of autologous peripheral blood lymphocytes (PLBs) in the preparation of CTL. Jochmus et al. (1997) J. Gen. Virol. 78, 1689-1695 describes the production of autologous CTL by employing pulsing dendritic cells with peptide or polypeptide, or via infection with recombinant virus. Hill et al. (1995) J. Exp. Med. 181, 2221-2228 and Jerome et al. (1993) J. Immunol. 151, 1654-1662 make use of B cells in the production of autologous CTL. In addition, macrophages pulsed with peptide or polypeptide, or infected with recombinant virus, may be used in the preparation of autologous CTL. S. Walter et al. Cutting edge: predetermined avidity of human CD8 T cells expanded on calibrated MHC/anti-CD28-coated microspheres. J. Immunol. 2003 Nov. 15; 171(10): 4974-8 describe the in vitro priming of T cells by using artificial antigen presenting cells, which is also a suitable way for generating T cells against the peptide of choice.

Allogeneic cells may also be used in the preparation of CTL and this method is described in detail in WO 97/26328, incorporated herein by reference. For example, in addition to *Drosophila* cells and T2 cells, other cells may be used to present antigens such as CHO cells, baculovirus-infected insects cells, bacteria, yeast, vaccinia-infected target cells. In addition plant viruses may be used (see, for example, Porta et al. (1994) Virology 202, 449-955), which describes the development of cowpea mosaic virus as a high-yielding system for the presentation of foreign peptides.

The activated CTL that are directed against the peptides of the invention are useful in therapy. Thus, a further aspect of the invention provides activated CTL obtainable by the foregoing methods of the invention.

A still further aspect of the invention provides activated CTL that selectively recognise a cell that aberrantly expresses a polypeptide comprising an amino acid sequence of the invention. Preferably, the CTL recognises the cell by interacting with the HLA/peptide-complex (for example, binding). The CTL are useful in a method of killing target cells in a patient, the method comprising targeting cells that aberrantly express a polypeptide comprising an amino acid sequence of the invention wherein the patient is administered an effective number of the activated CTL. The CTL that are administered to the patient may be derived from the patient and activated as described above (i.e. they are autologous CTL). Alternatively, the CTL are not from the patient but are from another individual. Of course, it is preferred if the individual is a healthy individual. By "healthy individual" the inventors mean that the individual is generally in good health, preferably has a competent immune system and, more preferably, is not suffering from any disease which can be readily tested for, and detected.

The activated CTL express a T-cell receptor (TCR), that is involved in recognising cells that express the aberrant polypeptide. It is useful if the cDNA encoding the TCR is cloned from the activated CTL and transferred into a further CTL for expression.

In vivo, the target cells for the CD4-positive CTL according to the present invention can be cells of the tumour (which sometimes express MHC class II) and/or stromal cells surrounding the tumour (tumour cells) (which sometimes also express MHC class II).

The TCRs of CTL clones of the invention specific for the peptides of the invention are cloned. The TCR usage in the CTL clones is determined using (i) TCR variable region-specific monoclonal antibodies and (ii) RT PCR with primers specific for Va and Vp gene families. A cDNA library is prepared from poly-A mRNA extracted from the CTL clones. Primers specific for the C-terminal portion of the TCR a and P chains and for the N-terminal portion of the identified Va and P segments are used. The complete cDNA for the TCR a chain is amplified with a high fidelity DNA polymerase and the amplified products cloned into a suitable cloning vector. The cloned a and P chain genes may be assembled into a single chain TCR by the method as described by Chung et al. (1994) Proc. Natl. Acad. Sci. USA 91, 12654-12658. In this single chain construct, the VaJ segment is followed by the V DJ segment, followed by the Cp segment followed by the transmembrane and cytoplasmic segment of the CD3 chain. This single chain TCR is then inserted into a retroviral expression vector (a panel of vectors may be used based on their ability to infect mature human CD8-positive T lymphocytes and to mediate gene expression: the retroviral vector system Kat is one preferred possibility (see Finer et al. (1994) Blood 83, 43). High titre amphotrophic retrovirus are used to infect purified CD8-positive or CD4-positive T lymphocytes isolated from the peripheral blood of tumour patients (following a protocol published by Roberts et al. (1994) Blood 84, 2878-2889, incorporated herein by reference). Anti-CD3 antibodies are used to trigger proliferation of purified $CD8^+$ T-cells, which facilitates retroviral integration and stable expression of single chain TCRs. The efficiency of retroviral transduction is determined by staining of infected $CD8^+$ T-cells with antibodies specific for the single chain TCR. In vitro analysis of transduced CD8-positive T-cells establishes that they display the same tumour-specific killing as seen with the allo-restricted CTL clone from which the TCR chains were originally cloned. Populations of transduced CD8-positive T-cells with the expected specificity may be used for adoptive immunotherapy of the tumour patients. Patients may be treated with in between $10^8$ to $10^{11}$ autologous, transduced CTL. Analogously to CD8-positive, transduced CD4-positive T helper cells carrying related constructs can be generated.

Other suitable systems for introducing genes into CTL are described in Moritz et al. (1994) Proc. Natl. Acad. Sci. USA 91, 4318-4322, incorporated herein by reference. Eshhar et al. (1993) Proc. Natl. Acad. Sci. USA 90, 720-724 and Hwu et al (1993) J. Exp. Med. 178, 361-366 also describe the transfection of CTL. Thus, a further aspect of the invention provides a TCR that recognises a cell that aberrantly expresses a polypeptide comprising an amino acid sequence of the invention, the TCR being obtainable from the activated CTL.

In addition to the TCR, functionally equivalent molecules to the TCR are included in the invention. These include any molecule which is functionally equivalent to a TCR that can perform the same function as a TCR. In particular, such molecules include genetically engineered three-domain single-chain TCRs as made by the method described by Chung et al. (1994) Proc. Natl. Acad. Sci. USA 91, 12654-12658, incorporated herein by reference, and referred to above. The invention also includes a polynucleotide encoding the TCR or functionally equivalent molecule, and an expression vector encoding the TCR or functionally equivalent molecule thereof. Expression vectors that are suitable for expressing the TCR of the invention include those described above in respect of expression of the peptides of the invention.

It is, however, preferred that the expression vectors are ones that are able to express the TCR in a CTL following transfection.

A still further aspect of the invention provides a method of killing target cells in a patient that target cells aberrantly expressing a polypeptide comprising an amino acid sequence of the invention, the method comprising the steps of (1) obtaining CTL from the patient; (2) introducing into said cells a polynucleotide encoding a TCR, or a functionally equivalent molecule, as defined above; and (3) introducing the cells produced in step (2) into the patient.

A still further aspect of the invention provides a method of killing target cells in a patient that target cells aberrantly expressing a polypeptide comprising a peptide of the present invention as discussed above the method comprising the steps of (1) obtaining antigen presenting cells, such as dendritic cells, from said patient; (2) contacting said antigen presenting cells with a peptide of the present invention, or with a polynucleotide encoding such a peptide, ex vivo; and (3) reintroducing the so treated antigen presenting cells into the patient.

Preferably, the antigen presenting cells are dendritic cells. Suitably, the dendritic cells are autologous dendritic cells that are pulsed with an antigenic peptide. The antigenic peptide may be any suitable antigenic peptide that gives rise to an appropriate T-cell response. T-cell therapy using autologous dendritic cells pulsed with peptides from a tumour associated antigen is disclosed in Murphy et al. (1996) The Prostate 29, 371-380 and Tjua et al (1997) The Prostate 32, 272-278.

In a further embodiment, the antigen presenting cells, such as dendritic cells, are contacted with a polynucleotide that encodes a peptide of the invention. The polynucleotide may be any suitable polynucleotide and is preferably capable of transducing the dendritic cell thereby resulting in the presentation of a peptide and induction of immunity.

Preferably, the polynucleotide may be comprised in a viral polynucleotide or virus. For example, adenovirus-transduced dendritic cells have been shown to induce antigen-specific antitumour immunity in relation to MUC1 (see Gong et al. (1997) Gene Ther. 4, 1023-1028). Similarly, adenovirus-based systems may be used (see, for example, Wan et al. (1997) Hum. Gene Ther. 8, 1355-1363); retroviral systems may be used (Specht et al. (1997) J. Exp. Med. 186, 1213-1221 and Szabolcs et al. (1997) Blood particle-mediated transfer to dendritic cells may also be used (Tuting et al. (1997) Eur. J. Immunol. 27, 2702-2707); and RNA may also be used (Ashley et al. (1997) J. Exp. Med. 186, 1177 1182).

It will be appreciated that, with respect to the methods of killing target cells in a patient, it is particularly preferred that the target cells are cancer cells, more preferably renal or colon cancer cells.

More particularly, preferably, the patients who are treated by the methods of the invention have the HLA-DR haplotype. Thus, in a preferred embodiment the HLA haplotype of the patient is determined prior to treatment. HLA haplotyping may be carried out using any suitable method. Such methods are well known in the art.

The invention includes the use of the peptides of the invention (or polynucleotides encoding them) for active in vivo vaccination; for manipulation of autologous dendritic cells in vitro followed by introduction of the so-manipulated dendritic cells in vivo to activate CTL responses; to activate autologous CTL in vitro followed by adoptive therapy (i.e. the so-manipulated CTL are introduced into the patient); and to activate CTL from healthy donors (MHC matched or mismatched) in vitro followed by adoptive therapy.

In a preferred embodiment, vaccines of the present invention are administered to a host either alone or in combination with another cancer therapy to inhibit or suppress the formation of tumours.

Peptide vaccines of the present invention may be administered without adjuvant. The peptide vaccine may also be administered with an adjuvant such as BCG or alum. Other suitable adjuvants include Aquila's QS21 stimulon (Aquila Biotech, Worcester, Mass., USA), which is derived from saponin, mycobacterial extracts and synthetic bacterial cell wall mimics, and proprietary adjuvants such as Ribi's Detox. Quil A, another saponin derived adjuvant, may also be used (Superfos, Denmark). Other adjuvants such as CpG oligonucleotides, stabilized RNA, Imiquimod (commercially available under the tradename Aldara™ from 3M Pharma, U.S.A.), Incomplete Freund's Adjuvant (commercially available as Montanide ISA-51 from Seppic S.A., Paris, France), liposomal formulations or GM-CSF may also be useful. It may also be useful to give the peptide conjugated to keyhole limpet hemocyanin, preferably also with an adjuvant.

Peptides according to the invention can also be used as diagnostic reagents. Using the peptides it can be analysed, whether in a CTL-population. CTLs are present that are specifically directed against a peptide or are induced by a therapy. Furthermore, the increase of precursor T-cells can be tested with those peptides that have reactivity against the defined peptide. Furthermore, the peptide can be used as marker in order to monitor the progression of the disease of a tumour that expresses the antigen from which the peptide is derived.

In the attached Table 1 the peptides as identified are listed. In addition, in the Table the proteins are designated, from which the peptide is derived, and the respective position of the peptide in the respective protein. Furthermore the respective Acc-Numbers are given that relate to the Genbank of the "National Centre for Biotechnology Information" of the National Institute of Health (see http: www.ncbi.nlm.nih.gov).

In another preferred embodiment peptides of the present invention are used for staining of leukocytes, in particular of T-lymphocytes. This use is of particular advantage if it should be proven, whether in a CTL-population specific CTLs are present that are directed against a peptide. Furthermore the peptide can be used as marker for determining the progression of a therapy in a tumourous disease or disorder.

In another preferred embodiment peptides of the present invention are used for the production of an antibody. Polyclonal antibodies can be obtained in a standard fashion by immunisation of animals via injection of the peptide and subsequent purification of the immune globulin. Monoclonal antibodies can be produced according to standard protocols such as described, for example, in Methods Enzymol. (1986), 121, Hybridoma technology and monoclonal antibodies.

The invention also provides a pharmaceutical composition that contains one or more peptides according to the invention. This composition is used for parenteral administration, such as subcutaneous, intradermal, intramuscular or oral administration. For this, the peptides are dissolved or suspended in a pharmaceutically acceptable, preferably aqueous carrier. In addition, the composition can contain excipients, such as buffers, binding agents, blasting agents, diluents, flavours, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, 3. Ed., 2000, American Pharmaceutical Association and pharmaceutical press. The composition can be used for a prevention, prophylaxis and/or therapy of tumourous diseases.

The pharmaceutical preparation, containing at least one of the peptides of the present invention comprising any of the SEQ ID No. 1 to SEQ ID No. 49 is administered to a patient that suffers from a tumourous disease that is associated with the respective peptide or antigen. By this, a CTL-specific immune response can be triggered.

In another aspect of the present invention, a combination of two or several peptides according to the present invention can be used as vaccine, either in direct combination or within the same treatment regimen. Furthermore, combinations with other peptides, for example MHC class II specific peptides can be used. The person of skill will be able to select preferred combinations of immunogenic peptides by testing, for example, the generation of T-cells in vitro as well as their efficiency and overall presence, the proliferation, affinity and expansion of certain T-cells for certain peptides, and the functionality of the T-cells, e.g. by analyzing the production of IFN-γ (see also examples below), IL-12 or Perforin. Usually, the most efficient peptides are then combined as a vaccine for the purposes as described above.

A preferred vaccine will contain 2, 3, 4, 5, 6, 7, 8, 9, 10, 11, 12, 13, 14 or 15 different peptides, preferably 4, 5, 6 or 7 different peptides, and most preferably 6 different peptides.

Finally, the vaccine can be dependent from the specific type of cancer that the patient to be treated is suffering from as well as the status of the disease, earlier treatment regimens, the immune status of the patient, and, of course, the HLA-haplotype of the patient.

It has been shown that the 80 N-terminal amino acids of Ii are sufficient to direct proteins into the class II processing pathway (Sanderson, S., Frauwirth, K. & Shastri, N. (1995) Proc. Natl. Acad. Sci. U.S.A 92, 7217-7221, Wang, R. F., Wang, X., Atwood, A. C., Topalian, S. L. & Rosenberg, S. A. (1999) Science 284, 1351-1354).

The identification of T-helper cell epitopes of tumour associated antigens remains an important task in anti-tumour immunotherapy. Here the inventors report a generally applicable method and peptides that have been derived from differential peptide analysis by MS to identify naturally processed and presented MHC class II ligands of tumour associated antigens. This approach combines for the first time a transfection step of APC with a vector encoding for a fusion protein between the Ii chain and the Ag of interest, elution of the HLA-bound peptides and MS identification of the Ag-derived peptides presented by the transfectant by comparison to the non-transfected cells. Moreover, the inventors could validate the method by showing that T-cells induced against the identified peptide specifically recognise transfectants overexpressing the cognate Ag. Although the identified peptides still have to be tested for their immunogenicity in vivo, our approach leads to the exact characterisation of naturally processed MHC class II ligands. Thus, the inventors avoid testing either synthetic overlapping peptides of tumour associated antigens, or a broad range of peptides selected by epitope prediction, which is less accurate as compared to class I epitope prediction. In contrast to laborious T-cell assays, which might lead to the identification of cryptic T-cell epitopes unable to induce T-cell activation in vivo (Anderton, S. M., Viner, N. J., Matharu, P., Lowrey, P. A. & Wraith, D.C. (2002) Nat. Immunol. 3, 175-181), the work can be focused on the few peptides that are found to be presented. Moreover, using this method it is not necessary to produce the recombinant Ag or to possess Ag-expressing tumour cell lines in order to prove that the peptides are naturally processed.

The inventors used the N-terminus of Ii to direct tumour associated antigens into the class II processing compartment of EBV-transformed B cells. In order to achieve this, the inventors constructed a versatile vector to express any antigen as a fusion protein with Ii and which helped determine the expression level of the protein in transfected cells by Western blot analysis. It has already been shown that the N-terminus of Ii is sufficient to target proteins into the class II processing compartment. But until now this has only been described in a model using ovalbumin (Sanderson, S., Frauwirth, K. & Shastri, N. (1995) Proc. Natl. Acad. Sci. U.S.A 92, 7217-7221), in order to identify unknown Ag using fusion protein-encoding cDNA libraries (Wang, R. F., Wang, X., Atwood, A. C., Topalian, S. L. & Rosenberg, S. A. (1999) Science 284, 1351-1354) or to confirm the specificity of known T-cell clones (Chaux, P., Vantomme, V., Stroobant, V., Thielemans, K., Corthals, J., Luiten, R., Eggermont, A. M., Boon, T. & van der, B. P. (1999) J. Exp. Med. 189, 767-778). To the inventors' knowledge this method has never been used before to identify naturally presented MHC class II bound peptides of known tumour associated antigens. The differential analysis of class II ligands of transfected and non-transfected cells by MALDI-MS and the further characterisation of the differentially expressed peptides by ESI-MS results in a straightforward method for identifying class II ligands of antigens of interest. Transfection of cells with keratin 18 fusion proteins proved that the inventors' method is generally applicable for antigens of interest, again, the inventors were also able to describe an HLA-DR-presented peptide from a model transgene, keratin 18.

The identification of helper T-cell epitopes of TAA remains an important task in anti-tumor immunotherapy. Until now, different strategies for the identification of class II peptides from TAA have been carried out, ranging from the incubation of APCs with the antigen of interest in order to be taken up and processed (Chaux, P., V. Vantomme, V. Stroobant, K. Thielemans, J. Corthals, R. Luiten, A.M. Eggermont, T. Boon, and B. P. van der Bruggen. 1999. Identification of MAGE-3 epitopes presented by HLA-DR molecules to CD4(+) T lymphocytes. *J. Exp. Med.* 189:767-778), to various transfection strategies with fusion proteins (Dengjel, J., P. Decker, O. Schoor, F. Altenberend, T. Weinschenk, H. G. Rammensee, and S. Stevanovic. 2004. Identification of a naturally processed cyclin D1 T-helper epitope by a novel combination of HLA class II targeting and differential mass spectrometry. *Eur. J. Immunol.* 34:3644-3651). All these methods are very time-consuming and it often remained unclear, if the identified HLA ligands are actually presented in vivo by human tissue. The inventors could show for the first time that it is possible to isolate HLA class II ligands directly from dissected solid tumors, thus identifying the peptides that are presented by tumors and surrounding tissue in vivo, which can hence be recognized by T-cells bearing the appropriate T-cell receptor and which simultaneously express the co-stimulatory ligand CD4 on their cell surface. Among the proteins functioning as a source for endogenously processed HLA class II ligands, several housekeeping and immuno-relevant proteins were identified. However, peptides from TAA could also be detected, leading to a straightforward approach for the identification of in vivo relevant class II ligands of TAA.

The inventors identified three ligands accounting for one core sequence from IGFBP3 and one ligand from MMP7. The inventors found these proteins to be over-expressed in renal cell carcinomas, in addition, they have been described as tumor-associated (Miyamoto, S., K. Yano, S. Sugimoto, G. Ishii, T. Hasebe, Y. Endoh, K. Kodama, M. Goya, T. Chiba, and A. Ochiai. 2004. Matrix metalloproteinase-7 facilitates insulin-like growth factor bioavailability through its proteinase activity on insulin-like growth factor binding protein 3. *Cancer Res.* 64:665-671; Sumi, T., T. Nakatani, H. Yoshida, Y. Hyun, T. Yasui, Y. Matsumoto, E. Nakagawa, K. Sugimura, H. Kawashima, and O. Ishiko. 2003. Expression of matrix metalloproteinases 7 and 2 in human renal cell carcinoma. *Oncol. Rep.* 10:567-570; Cheung, C. W., D. A. Vesey, D. L. Nicol, and D. W. Johnson. 2004. The roles of IGF-I and IGFBP-3 in the regulation of proximal tubule, and renal cell carcinoma cell proliferation. *Kidney Int.* 65:1272-1279). These peptides bound promiscuously to HLA class II molecules and were able to activate CD4-positive T-cells from different healthy donors. Thus, the inventors' approach will be helpful in the identification of new class II peptide candidates from TAA for use in clinical vaccination protocols.

The invention in a further aspect relates to a method of killing target cells in a patient, wherein the target cells express a polypeptide comprising an amino acid sequence as provided herein, the method comprising administering to the patient an effective amount of a peptide according to the present invention or a nucleic acid according to the present invention or an expression vector according to the present invention, wherein the amount of said peptide or amount of said nucleic acid or amount of said expression vector is effective to provoke an anti-target cell immune response in said patient.

The invention in a further aspect relates to a method of killing target cells in a patient, wherein the target cells express a polypeptide comprising an amino acid sequence according to the present invention, the method comprising administering to the patient an effective number of cytotoxic T lymphocytes (CTL) as defined according to the present invention.

The invention in a further aspect relates to a method of killing target cells in a patient, wherein the target cells express a polypeptide comprising an amino acid sequence according to the present invention, the method comprising the steps of (1) obtaining cytotoxic T lymphocytes (CTL) from the patient; (2) introducing into said cells a nucleic acid encoding a T cell receptor (TCR), or a functionally equivalent molecule, as defined according to the present invention; and (3) introducing the cells produced in step (2) into the patient.

Preferably, the target cells are cancer cells. More preferably, the cancer is leukemia or lymphoma that expresses a polypeptide which comprises an amino acid sequence of the present invention.

It has been surprisingly found in the context of the present invention that tumour cells of solid tumours, in contrast to healthy cells of the same tissue, express human HLA class II molecule on their surface. This fact has been described only once in Brasanac et al. (Brasanac D, Markovic-Lipkovski J, Hadzi-Djokic J, Muller G A, Muller C A. Immunohistochemical analysis of HLA class II antigens and tumor infiltrating mononuclear cells in renal cell carcinoma: correlation with clinical and histopathological data. Neoplasma. 1999; 46(3): 173-8.), where cryostat sections of 37 renal cell carcinomas (RCC)—25 clear cell type, 10 granular and 2 chromophobe—were studied with indirect immunoperoxidase method applying monoclonal antibodies (MoAb) to HLA-DR, -DP and -DQ antigens for analysis of HLA class II antigens, and anti-CD14, -CD3, -CD4 and -CD8 MoAb for tumour infiltrating mononuclear cells (TIM). The number of positive cells was estimated semiquantitatively and results of immunohistochemical investigation were correlated with clinical (patient age and sex, tumour size and TNM stage) and histopathological (cytology, histology, grade) characteristics of RCC. All RCC expressed HLA-DR, 92%-DQ and 73%-DP antigens with level of expression in hierarchy -DR>-DQ>-DP, but no statistically important correlation could be established with any of the histopathological or clinical parameters analyzed. Monocytes were more abundant than T lymphocytes and CD4+ than CD8+ T cells, whereas tumours with T lymphocyte predominance and approximately equal number of CD4+ and CD8+ T cells had greatest average diameter. Inadequate activation of T lymphocytes by tumour cells (despite capability of antigen presentation) could be the reason for association of parameters which indicates more aggressive tumour behaviour with aberrant HLA class II antigen expression on RCC.

It should be understood that the features of the invention as disclosed and described herein can be used not only in the respective combination as indicated but also in a singular fashion without departing from the intended scope of the present invention.

The invention will now be described in more detail by reference to the following Figures, the Sequence listing, and the Examples. The following examples are provided for illustrative purposes only and are not intended to limit the invention.

SEQ ID NO: 1 to SEQ ID NO: 49 show peptide sequences of T-cell epitope containing peptides that are presented by MHC class II according to the present invention.

SEQ ID NO: 50 to SEQ ID NO: 79 show peptide sequences of Table 3.

TABLE 1

Peptide sequences aligned according to the motif of HLA-DRB1*0101.
DRB1Peptides with scores greater than 19 were considered as *0101 binders

| | Sequence -3-2-1 1 2 3 4 5 6 7 8 9 +1+2+3 | Gene Symbol | Acc. Nr. | Position | SYFPEITHI Score | SEQ ID NO: |
|---|---|---|---|---|---|---|
| 1. | S Q D D I K G I Q K L Y G K R S | MMP7 | NP_002414 | 247-262 | 35 | SEQ ID NO: 33 |
| 2. | N K Q K P I T P E T A E K L A R D | CDC42 | NP_426359 | 132-148 | 26 | SEQ ID NO: 2 |
| 3. | D D P S T I E K L A K N K Q K P | CDC42 | NP_426359 | 121-136 | 19 | SEQ ID NO: 3 |
| 4. | N P L K I F P S K R I L R R H | CDH3 | NP_001784 | 91-105 | 27 | SEQ ID NO: 4 |
| 5. | E T G W L L L N K P L D R | CDH3 | NP_001784 | 163-175 | 19 | SEQ ID NO: 5 |
| 6. | D N E L Q E M S N Q G S K | CLU | NP_001822 | 80-92 | 24 | SEQ ID NO: 6 |
| 7. | A A G L L S T Y R A F L S S H | COL15A1 | NP_001846 | 1243-1257 | 24 | SEQ ID NO: 7 |
| 8. | A P S L R P K D Y E V D A T L K S L N N Q | COL1A2 | NP_000080 | 1125-1145 | 25 | SEQ ID NO: 8 |
| 9. | G P V D E V R E L Q K A I G A V P | CTSD | NP_001900 | 303-319 | 26 | SEQ ID NO: 9 |
| 10. | I N H V V S V A G W G I S D G | CTSZ | NP_001327 | 239-253 | 33 | SEQ ID NO: 10 |
| 11. | V P D D R D F E P S L G P V C P F R | DCN | NP_001911 | 40-57 | 23 | SEQ ID NO: 11 |
| 12. | L P Q S I V Y K Y M S I R S D R S V P S | EFEMP1 | NP_004096 | 389-408 | 30 | SEQ ID NO: 12 |
| 13. | I V H R Y M T I T S E R S V P A | EFEMP2 | NP_058634 | 343-358 | 30 | SEQ ID NO: 13 |
| 14. | K N G F V V L K G R P C K | EIF5A | NP_001961 | 27-39 | 28 | SEQ ID NO: 14 |
| 15. | I T G Y I I K Y E K P G S P P | FN1 | NP_002017 | 1930-1944 | 23 | SEQ ID NO: 15 |
| 16. | G A T Y N I I V E A L K D Q | FN1 | NP_002017 | 2134-2147 | 20 | SEQ ID NO: 16 |
| 17. | L T G Y R V R V T P K E K T G P | FN1 | NP_002017 | 1749-1764 | 21 | SEQ ID NO: 17 |
| 18. | I P G H L N S Y T I K G L K P G | FN1 | NP_002017 | 659-674 | 24 | SEQ ID NO: 18 |
| 19. | N L R F L A T T P N S L | FN1 | NP_997640 | 1908-1919 | 26 | SEQ ID NO: 19 |
| 20. | S N T D L V P A P A V R I L T P E | GDF15 | NP_004855 | 76-92 | 25 | SEQ ID NO: 20 |
| 21. | A E I L E L A G N A A R D N | H2AFJ | NP_808760 | 61-74 | 32 | SEQ ID NO: 21 |
| 22. | V K E P V A V L K A N R V W G A L | HEXB | NP_000512 | 153-169 | 32 | SEQ ID NO: 22 |
| 23. | T A E I L E L A G N A A R D N K | HIST3H2A | NP_254280 | 60-75 | 32 | SEQ ID NO: 23 |
| 24. | H P L H S K I I I I K K G H A K | IGFBP3 | NP_000589 | 166-181 | 25 | SEQ ID NO: 24 |

TABLE 1-continued

Peptide sequences aligned according to the motif of HLA-DRB1*0101.
DRB1Peptides with scores greater than 19 were considered as *0101 binders

| # | Sequence (-3-2-1 1 2 3 4 5 6 7 8 9 +1+2+3) | Gene Symbol | Acc. Nr. | Position | SYFPEITHI Score | SEQ ID NO: |
|---|---|---|---|---|---|---|
| 25. | H S K I I I I K K G H A K D S Q | IGFBP3 | NP_000589 | 169-184 | 28 | SEQ ID NO: 25 |
| 26. | R P K H T R I S E L K A E A V K K D | IGFBP5 | NP_000590 | 138-155 | 32 | SEQ ID NO: 26 |
| 27. | G P E D N V V I I Y L S R A G N P E | ISLR | NP_005536 | 380-397 | 26 | SEQ ID NO: 27 |
| 28. | S R P V I N I Q K T I T V T P N | ITGA6 | NP_000201 | 464-479 | 32 | SEQ ID NO: 28 |
| 29. | L D L S F N Q I A R L P S G L P V | LUM | NP_002336 | 189-205 | 30 | SEQ ID NO: 29 |
| 30. | K L P S V E G L H A I V V S D R | MAP2K1IP1 | NP_068805 | 12-27 | 32 | SEQ ID NO: 30 |
| 31. | D T S T L E M M H A P R C G | MMP12 | NP_002417 | 80-93 | 23 | SEQ ID NO: 31 |
| 32. | D Q N T I E T M R K P R C G N P D | MMP2 | NP_004521 | 90-106 | 20 | SEQ ID NO: 32 |
| 33. | N P G E Y R V T A H A E G Y T P S | AEBP1 | NP_001120 | 947-963 | 20 | SEQ ID NO: 1 |
| 34. | L D F L K A V D T N R A S V G | PLXDC2 | NP_116201 | 69-83 | 29 | SEQ ID NO: 34 |
| 35. | H G N Q I A T N G V V H V I D R | POSTN | NP_006466 | 213-228 | 23 | SEQ ID NO: 35 |
| 36. | R A I E A L H G H E L R P G | RBM14 | NP_006319 | 50-63 | 32 | SEQ ID NO: 36 |
| 37. | D P G V L D R M M K K L D T N S D | S100A11 | NP_005611 | 56-72 | 25 | SEQ ID NO: 37 |
| 38. | N E E E I R A N V A V V S G A P | SDCBP | NP_001007069 | 56-71 | 26 | SEQ ID NO: 38 |
| 39. | P A I L S E A S A P I P H | SDCBP | NP_001007068 | 29-41 | 24 | SEQ ID NO: 39 |
| 40. | K V I Q A Q T A F S A N P A | SDCBP | NP_001007070 | 14-27 | 30 | SEQ ID NO: 40 |
| 41. | N G A Y K A I P V A Q D L N A P S | SPP1 | NP_000573 | 185-201 | 19 | SEQ ID NO: 41 |
| 42. | T N G V V H V I T N V L Q P P A | TGFB1 | NP_000349 | 621-636 | 29 | SEQ ID NO: 42 |
| 43. | T T T Q L Y T D R T E K L R P E | TGFBI | NP_000349 | 116-131 | 23 | SEQ ID NO: 43 |
| 44. | G K K E Y L I A G K A E G D G | TIMP2 | NP_003246 | 106-120 | 25 | SEQ ID NO: 44 |
| 45. | M G E I A S F D K A K L K K T | TMSB10 | NP_066926 | 6-20 | 20 | SEQ ID NO: 45 |
| 46. | M A E I E K F D K S K L K K | TMSB4Y | NP_004193 | 6-19 | 19 | SEQ ID NO: 46 |
| 47. | V V S S I E Q K T E G A E K K | YWHAZ | NP_003397 | 61-75 | 22 | SEQ ID NO: 47 |

TABLE 1-continued

Peptide sequences aligned according to the motif of HLA-DRB1*0101.
DRB1Peptides with scores greater than 19 were considered as *0101 binders

| Sequence<br>-3-2-1 1 2 3 4 5 6 7 8 9 +1+2+3 | Gene<br>Symbol | Acc. Nr. | Position | SYFPEITHI<br>Score | SEQ ID<br>NO: |
|---|---|---|---|---|---|
| 48. H S K I I I I K K G H A K | IGFBP3 | NP_000589 | 169-181 | 25 | SEQ ID NO: 48 |
| 49. N P P S M V A A G S V V A A V | CCND1 | NP_444284 | 198-212 | 24 | SEQ ID NO: 49 |

EXAMPLES

Material and Methods

MHC class II immunohistology: tumors were fixed in 4% phosphate-buffered formaldehyde, embedded in paraffin, stained with hematoxylin-eosin and examined by light microscopy. Diagnosis of the RCC was carried out according to routine histopathological and immunohistological investigations (Fleming, S, and M. O'Donnell. 2000. Surgical pathology of renal epithelial neoplasms: recent advances and current status. *Histopathology* 36:195-202).

For immunohistological detection of MHC class II molecules or CD68 molecules, respectively, 5 μm paraffin-embedded tissue sections were pretreated with 10 mM citrate buffer, pH 6, followed by incubation either with a mouse anti-HLA-DR alpha-chain mAb (clone TAL.1B5, 1:50) or CD68 Ab (Clone PGM1, 1:50) (DAKO, Hamburg, Germany) or mouse IgG1 (2 μg/ml, BD Biosciences Pharmingen, San Diego, USA) and visualized using the Ventana iView DAB detection kit (Nexes System, Ventana Medical Systems, Illkirch, France). Tissue sections were counterstained with hematoxylin and finally embedded in Entellan.

Elution and molecular analysis of HLA-DR bound peptides: frozen tumor samples were processed as previously described (Weinschenk, T., C. Gouttefangeas, M. Schirle, F. Obermayr, S. Walter, O. Schoor, R. Kurek, W. Loeser, K. H. Bichler, D. Wernet, S. Stevanovic, and H. G. Rammensee. 2002. Integrated functional genomics approach for the design of patient-individual antitumor vaccines. *Cancer Res.* 62:5818-5827) and peptides were isolated according to standard protocols (Dengjel, J., H. G. Rammensee, and S. Stevanovic. 2005. Glycan side chains on naturally presented MHC class II ligands. *J Mass Spectrom.* 40:100-104) using the HLA-DR specific mAb L243 (Lampson, L. A. and R. Levy. 1980. Two populations of Ia-like molecules on a human B cell line. *J. Immunol.* 125:293-299).

Natural peptide mixtures were analyzed by a reversed phase Ultimate HPLC system (Dionex, Amsterdam, Netherlands) coupled to a Q-TOF I mass spectrometer (Waters, Eschborn, Germany), or by a reversed phase CapLC HPLC system coupled to a Q-TOF Ultima API (Waters) as previously described (Lemmel, C., S. Weik, U. Eberle, J. Dengjel, T. Kratt, H. D. Becker, H. G. Rammensee, and S. Stevanovic. 2004. Differential quantitative analysis of MHC ligands by mass spectrometry using stable isotope labeling. *Nat. Biotechnol.* 22:450-454). Fragment spectra were analyzed manually and automatically.

Gene expression analysis by high-density oligonucleotide microarrays: RNA isolation from tumor and autologous normal kidney specimens as well as gene expression analysis by Affymetrix Human Genome U133 Plus 2.0 oligonucleotide microarrays (Affymetrix, Santa Clara, Calif., USA) were performed as described previously (Krüger, T., O. Schoor, C. Lemmel, B. Kraemer, C. Reichle, J. Dengjel, T. Weinschenk, M. Müller, J. Hennenlotter, A. Stenzl, H. G. Rammensee, and S. Stevanovic. 2004. Lessons to be learned from primary renal cell carcinomas: novel tumor antigens and HLA ligands for immunotherapy. *Cancer Immunol. Immunother*). Data were analyzed with the GCOS software (Affymetrix). Pairwise comparisons between tumor and autologous normal kidney were calculated using the respective normal array as baseline. For RCC149 and RCC211 no autologous normal kidney array data were available. Therefore, pooled healthy human kidney RNA was obtained commercially (Clontech, Heidelberg, Germany) and used as the baseline for these tumors.

Maturation of DCs: DCs were prepared using blood from healthy donors. Briefly, PBMCs were isolated using standard gradient centrifugation (Lymphocyte Separation Medium, PAA Laboratories GmbH, Pasching, Austria) and plated at a density of $7\times10^6$ cells/ml in X-Vivo 15 medium. After 2 hours at 37° C., non-adherent cells were removed and adherent monocytes cultured for 6 days in X-Vivo medium with 100 ng/ml GM-CSF and 40 ng/ml IL-4 (AL-ImmunoTools, Friesoythe, Germany). On day 7, immature DCs were activated with 10 ng/ml TNF-α (R&D Systems, Wiesbaden, Germany) and 20 μg/ml poly(IC) (Sigma Aldrich, Steinheim, Germany) for 3 days.

Generation of antigen-specific CD4-positive T-cells: $10^6$ PBMCs per well were stimulated with $2\times10^5$ peptide pulsed (5 μg/ml) autologous DCs. Cells were incubated in 96-well plates (7 wells per donor and per peptide) with T-cell medium: supplemented RPMI 1640 in the presence of 10 ng/ml IL-12 (Promocell, Heidelberg, Germany). After 3 to 4 days of co-incubation at 37° C., fresh medium with 80 U/ml IL-2 (Proleukin, Chiron Corporation, Emeryville, Calif., USA) and 5 ng/ml IL-7 (Promocell) was added. Restimulations were done with autologous PBMCs plus peptide every 6 to 8 days.

Intracellular IFNγ staining: After 3 and 4 rounds of stimulation, PBMCs were thawed, washed twice in X-Vivo 15 medium, resuspended at $10^7$ cells/ml in T-cell medium and cultured overnight. On the next day, PBMCs, pulsed with 5 μg/ml peptide, were incubated with effector cells in a ratio of 1:1 for 6 h. Golgi-Stop (Becton Dickinson, Heidelberg, Germany) was added for the final 4 h of incubation.

Cells were analyzed using a Cytofix/Cytoperm Plus kit (Becton Dickinson) and CD4-FITC-(Immunotools), IFNγ-PE- and CD8-PerCP clone SK1-antibodies (Becton Dickinson). For negative controls, cells of seven wells were pooled and incubated either with irrelevant peptide or without peptide, respectively. Stimulation with PMA/Ionomycin was used for positive control. Cells were analyzed on a three-color FACSCalibur (Becton Dickinson).

Example 1

HLA Class II Expression by RCC

Under normal, non-inflammatory conditions, HLA class II molecules should only be expressed by cells of the hematopoietic system and by the thymic epithelium (Mach, B., V. Steimle, E. Martinez-Soria, and W. Reith. 1996. Regulation of MHC class II genes: lessons from a disease. *Annu. Rev. Immunol.* 14:301-331). The situation changes during inflammation. HLA class II expression can be induced in most cell types and tissues by IFNγ (Leib und Gut-Landmann, S., J. M. Waldburger, M. Krawczyk, L. A. Otten, T. Suter, A. Fontana, H. Acha-Orbea, and W. Reith. 2004. Mini-review: Specificity and expression of CIITA, the master regulator of MHC class II genes. *Eur. J. Immunol.* 34:1513-1525). As RCC incidence is often accompanied by inflammatory events (Blay, J. Y., J. F. Rossi, J. Wijdenes, C. Menetrier-Caux, S. Schemann, S, Negrier, T. Philip, and M. Favrot. 1997. Role of interleukin-6 in the paraneoplastic inflammatory syndrome associated with renal-cell carcinoma. *Int. J. Cancer* 72:424-430; Elsässer-Beile, U., M. Rindsfuser, T. Grussenmeyer, W. Schultze-Seemann, and U. Wetterauer. 2000. Enhanced expression of IFN-gamma mRNA in CD4(+) or CD8(+)tumour-infiltrating lymphocytes compared to peripheral lymphocytes in patients with renal cell cancer. *Br. J. Cancer* 83:637-641), class II molecules are indeed expressed in the vicinity of or by tumors, as has been reported.

Example 2

Immuno-Histochemical Staining of HLA Class II Molecules

Figure 1B:
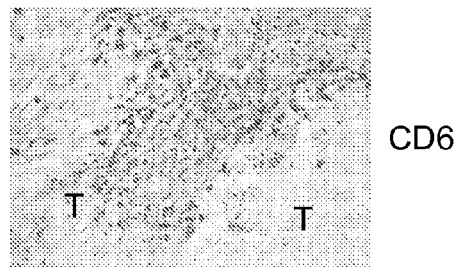
Figure 1C:
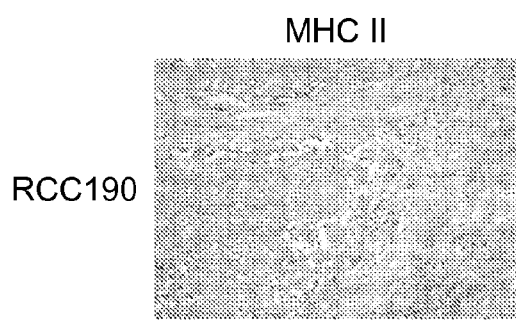
Figure 1D:
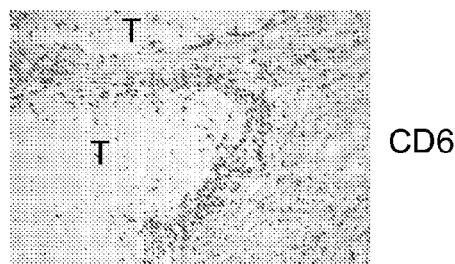
Figure 1E:
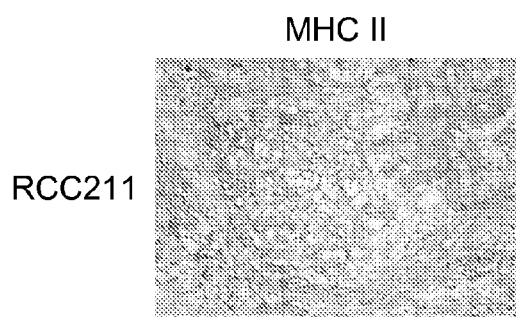
Figure 1F:
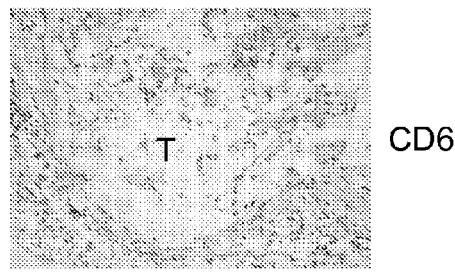
Figure 1G:
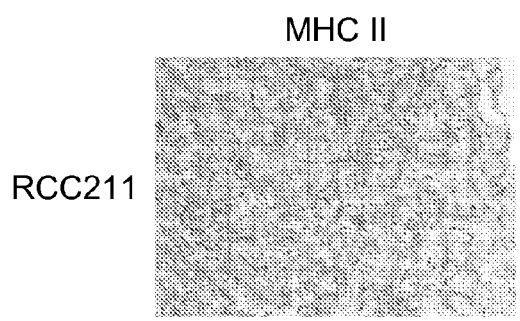
Figure 1H:
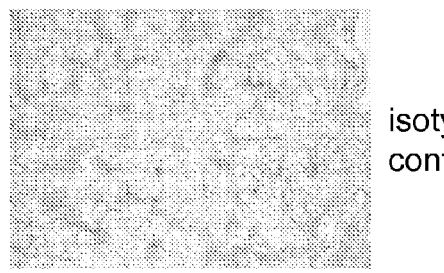

The inventors analyzed HLA class II expression of ten RCC specimens comprising histological clear cell and papillary renal carcinoma by immuno-histochemical staining and found that all investigated samples revealed class II positive tumor cells. As exemplified in FIG. 1A, a pronounced HLA class II expression was often detected at the margin of the tumor. In these areas the inventors observed a close spatial correlation of HLA positive tumor cells with tumor infiltrating immune cells as illustrated by the visualization of CD68-positive macrophages in a serial tissue section (FIG. 1B). In RCC revealing a more papillary architecture, the expression of HLA class II molecules was more evenly distributed throughout the tumor (FIGS. 1C, E, G). The comparison of the HLA class II and CD68 immuno-histochemical staining patterns in serial tissue sections clearly demonstrates that in addition to macrophages, tumor cells also express HLA class II (FIGS. 1C,D and E,F). It has been shown that IFNγ producing CD4-positive $T_{H1}$ cells as well as Natural Killer (NK) cells infiltrate RCC (Cozar, J. M., J. Canton, M. Tallada, A. Concha, T. Cabrera, F. Garrido, and O. F. Ruiz-Cabello. 2005. Analysis of NK cells and chemokine receptors in tumor infiltrating CD4 T lymphocytes in human renal carcinomas. *Cancer Immunol. Immunother*). As class II positive tumor cells were found predominantly in outer parts of dissected tumors, one could speculate that leukocytes attracted by the tumor produce IFNγ which acts on neighboring malignant cells. The abnormal expression of HLA class II molecules in neoplastic tissue is not restricted to RCC, it can also be detected in TCC and CCA. FIG. 4 shows immuno-histochemical staining of sampled tissue from human adenocarcinoma of the colon.

Example 3

Analysis of Expression of IFNγ and Gene Transcripts Induced by IFNγ

Additionally, the inventors investigated HLA class II expression by comparative gene expression analysis using oligonucleotide microarrays. With this technique the inventors were able to assess the overall HLA class II expression in the dissected tumors regardless of the expressing cell types. The inventors analyzed differential expression in four tumors, RCC149, RCC180, RCC190, and RCC211, compared with normal reference kidney. In all four tumors, genes encoding HLA class II molecules were found to be over-expressed (Table 2). One possible reason for this might be an induced expression by IFNγ and for this reason the inventors looked for other genes known to be up-regulated by interferons (Kolchanov, N. A., E. V. Ignatieva, E. A. Ananko, O. A. Podkolodnaya, I. L. Stepanenko, T. I. Merkulova, M. A. Pozdnyakov, N. L. Podkolodny, A. N. Naumochkin, and A. G. Romashchenko. 2002. Transcription Regulatory Regions Database (TRRD): its status in 2002. *Nucleic Acids Res.* 30:312-317). Interestingly, a considerable number of such genes were found to be over-expressed in one or more tumor samples. Table 2 shows interferon-inducible genes which were up-regulated reproducibly in all four samples, in accordance with the inventors' earlier findings (Weinschenk, T., C. Gouttefangeas, M. Schirle, F. Obermayr, S. Walter, O. Schoor, R. Kurek, W. Loeser, K. H. Bichler, D. Wernet, S. Stevanovic, and H. G. Rammensee. 2002. Integrated functional genomics approach for the design of patient-individual antitumor vaccines. *Cancer Res.* 62:5818-5827). Among them are LMP2, LMP7, and MECL1—proteins that are exchanged against constitutive subunits of the large proteolytic holoenzyme residing in the cytosol, the proteasome, to form the immunoproteasome. The exchange of normally expressed proteolytic subunits of the proteasome against IFNγ-inducible subunits is a hallmark process in an interferon-rich environment. Additionally, IFNγ was directly assessed by quantitative real-time (RT) PCR (TaqMan). The tumors displayed in Table 2 showed a 5- to 60-fold IFNγ mRNA over-expression compared with the autologous normal RNA samples from the same donor (data not shown). Thus, the inventors' results indicate that IFNγ might play an important role in RCC and be the reason for abundant class II expression.

TABLE 2 mRNA expression of interferon-inducible genes.
Expression in tumour samples was compared with autologous normal kidney (RCC180, RCC190) or pooled healthy kidney (RCC149, RCC211). All genes showed an "increase" in the change-call algorithm of the GCOS software for all four tumours and have been described as interferon-inducible.

| Gene Symbol | Entrez GeneID | Gene Title | -fold over-expression tumor vs. normal | | | |
|---|---|---|---|---|---|---|
| | | | RCC149 | RCC180 | RCC190 | RCC211 |
| HLA-DPA1 | 3113 | major histocompatibility complex, class II, DP alpha 1 | 3.5 | 3.7 | 4.9 | 13.9 |
| HLA-DPB1 | 3115 | major histocompatibility complex, class II, DP beta 1 | 2.6 | 2.5 | 2.8 | 14.9 |
| HLA-DQB1 | 3119 | major histocompatibility complex, class II, DQ beta 1 | 4.3 | 4.0 | 6.5 | 5.3 |
| HLA-DRB1 | 3123 | major histocompatibility complex, class II, DR beta 1 | 1.2 | 1.9 | 2.8 | 4.3 |
| CXCL10 | 3627 | chemokine (C-X-C motif) ligand 10 | 1.1 | 3.2 | 10.6 | 24.3 |
| FCGR1A | 2209 | Fc fragment of IgG, high affinity Ia, receptor for (CD64) | 6.5 | 2.6 | 12.1 | 29.9 |
| IFI16 | 3428 | interferon, gamma-inducible protein 16 | 8.6 | 3.0 | 4.3 | 11.3 |
| IFI44 | 10561 | interferon-induced protein 44 | 2.8 | 1.4 | 2.5 | 2.8 |
| OAS1 | 4938 | 2',5'-oligoadenylate synthetase 1, 40/46 kDa | 3.5 | 2.3 | 2.6 | 5.3 |
| PSMB8 | 5696 | proteasome subunit, beta type, 8 (LMP7) | 2.6 | 4.3 | 6.1 | 6.5 |
| PSMB9 | 5698 | proteasome subunit, beta type, 9 (LMP2) | 4.3 | 7.5 | 6.5 | 16.0 |
| PSMB10 | 5699 | proteasome subunit, beta type, 10 (MECL1) | 3.2 | 2.5 | 5.3 | 13.0 |
| SP100 | 6672 | nuclear antigen Sp100 | 4.0 | 1.1 | 1.5 | 2.8 |
| TAP1 | 6890 | transporter 1, ATP-binding cassette, sub-family B (MDR/TAP) | 2.5 | 2.8 | 6.5 | 8.0 |
| VCAM1 | 7412 | vascular cell adhesion molecule 1 | 5.7 | 5.3 | 3.2 | 12.1 |

Example 4

HLA-DR Ligands Isolated from Cancer Tissue

Figure 5A:
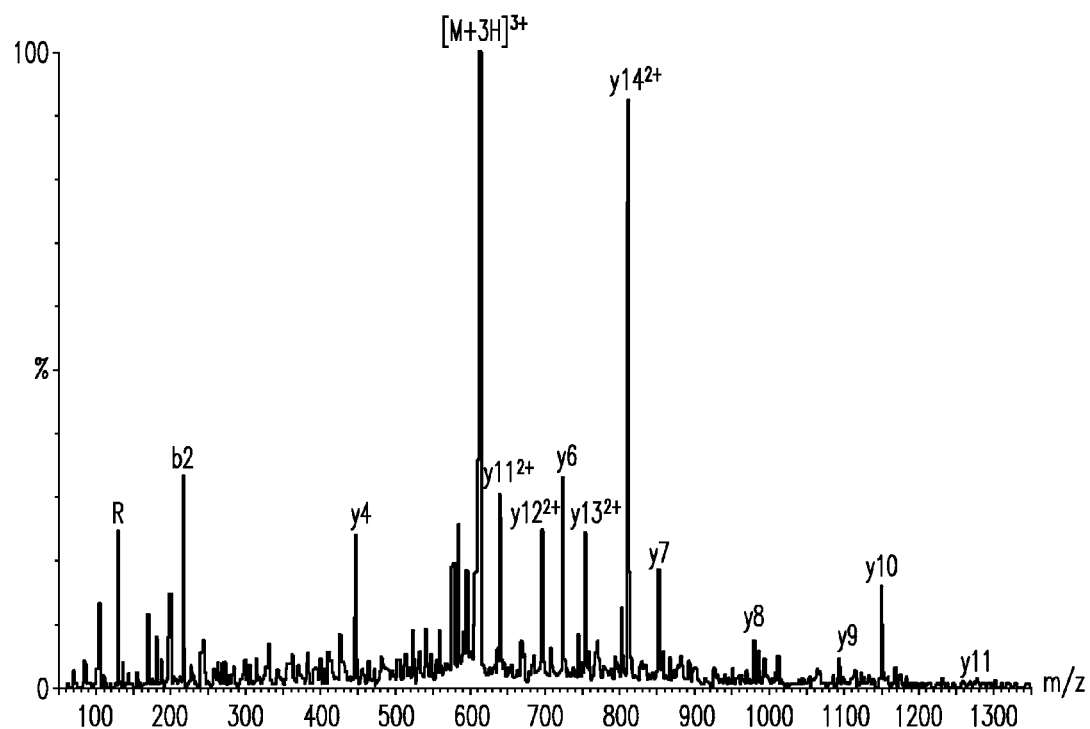
FIGS. 5a and 5b show the identification of peptide sequence of peptides eluted from HLA-Class II molecules isolated from primary human tumor tissue by mass spectroscopy.
Figure 5B:
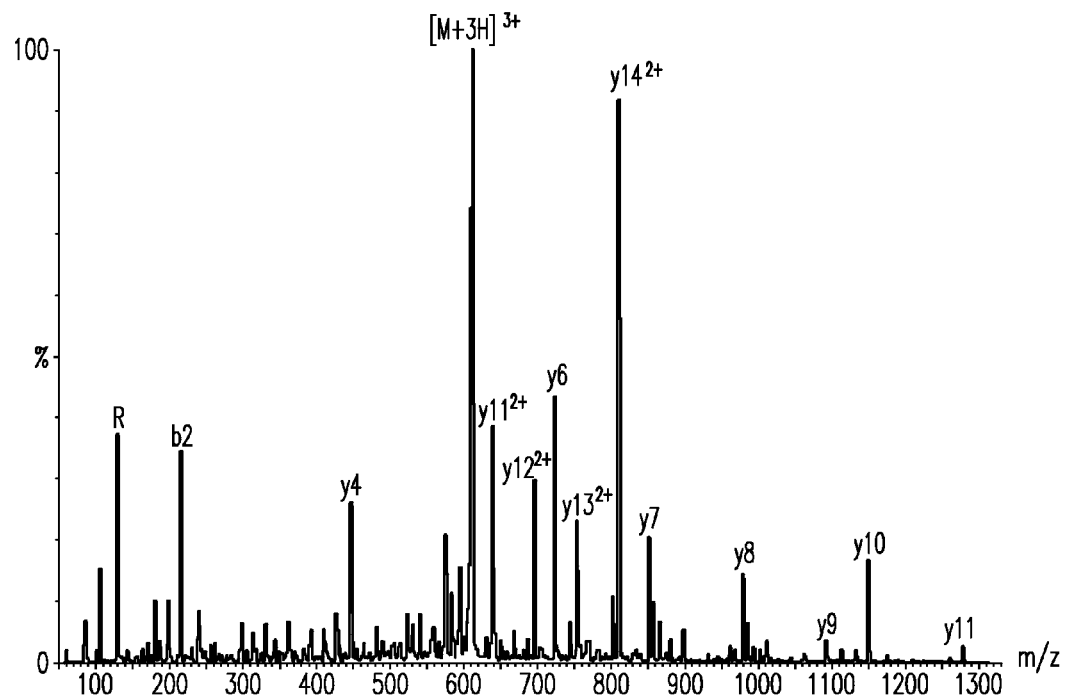

According to publicly available data, peptides bound by HLA class II molecules expressed in solid tumor tissue have so far not been isolated or identified by others. The inventors analyzed ten different RCC, three CCA and one TCC samples, and were able to isolate HLA-DR ligands from all samples, amounting to 453 peptides in total (data not shown). Peptide sequences were determined by coupling chromatographic separation and tandem-mass spectrometric analysis (LC-MS/MS), as previously described (Weinschenk, T., C. Gouttefangeas, M. Schirle, F. Obermayr, S. Walter, O. Schoor, R. Kurek, W. Loeser, K. H. Bichler, D. Wernet, S. Stevanovic, and H. G. Rammensee. 2002. Integrated functional genomics approach for the design of patient-individual antitumor vaccines. *Cancer Res.* 62:5818-582; Schirle M, Keilholz W, Weber B, Gouttefangeas C, Dumrese T, Becker H D, Stevanovic S, Rammensee H G. Identification of tumor-associated MHC class I ligands by a novel T-cell-independent approach. *Eur J. Immunol.* 2000; 30(8):2216-25). An example for the de novo sequencing of peptides by LC-MS/MS is given in FIGS. 5a and 5b. The deduced primary amino acid sequences of collision fragments annotated in FIGS. 5a and 5b is included in Table 5. The tumor specimens differed in their HLA genotypes, in weight and in the total number of identified HLA ligands. Table 3 shows a representative list of peptides and corresponding source proteins identified from one exemplary tumor sample, RCC190. Peptides were isolated from HLA class II molecules of cells as was previously described (Dengjel, J., P. Decker, O. Schoor, F. Altenberend, T. Weinschenk, H. G. Rammensee, and S. Stevanovic. 2004. Identification of a naturally processed cyclin D1 T-helper epitope by a novel combination of HLA class II targeting and differential mass spectrometry. *Eur. J. Immunol.* 34:3644-3651).

TABLE 3

Example list of HLA-DR ligands isolated from RCC190.
Shown are the core sequences of HLA-DR ligands isolated from
RCC190 (HLA-DRB1*11, DRB1*15, DRB3, DRB5).

| Gene Symbol | Entrez GeneID | Peptide Sequence (SEQ ID NO:) | Gene Title |
|---|---|---|---|
| ACTG1 | 71 | WISKQEYDESGPSIVHRKCF (SEQ ID NO: 50) | actin, gamma 1 propeptide |

TABLE 3-continued

Example list of HLA-DR ligands isolated from RCC190.
Shown are the core sequences of HLA-DR ligands isolated from
RCC190 (HLA-DRB1*11, DRB1*15, DRB3, DRB5).

| Gene Symbol | Entrez GeneID | Peptide Sequence (SEQ ID NO:) | Gene Title |
|---|---|---|---|
| ALB | 213 | LKKYLYEIARRHP (SEQ ID NO: 51) | albumin precursor |
| ALB | 213 | TLVEVSRNLGKVG (SEQ ID NO: 52) | albumin precursor |
| ALB | 213 | TPTLVEVSRNLGKVGS (SEQ ID NO: 53) | albumin precursor |
| APOA2 | 336 | EKSKEQLTPLIKKAGTELVNF (SEQ ID NO: 54) | apolipoprotein A-II precursor |
| APOB | 338 | YPKSLHMYANRLLDHR (SEQ ID NO: 55) | apolipoprotein B precursor |
| C1R | 715 | EPYYKMQTRAGSRE (SEQ ID NO: 56) | complement component 1, r subcomponent |
| C4B | 721 | APPSGGPGFLSIERPDSRPP (SEQ ID NO: 57) | complement component 4B proprotein |
| C4BPA | 722 | FGPIYNYKDTIVFK (SEQ ID NO: 58) | complement component 4 binding protein, alpha |
| CALR | 811 | SPDPSIYAYDNF (SEQ ID NO: 59) | Calreticulin precursor |
| CALR | 811 | EPPVIQNPEYKGEWKPRQIDNPD (SEQ ID NO: 60) | Calreticulin precursor |
| CFL1 | 1072 | GVIKVFNDMKVRK (SEQ ID NO: 61) | cofilin 1 (non-muscle) |
| CPE | 1363 | APGYLAITKKVAVPY (SEQ ID NO: 62) | carboxypeptidase E precursor |
| FCGBP | 8857 | ASVDLKNTGREEFLTA (SEQ ID NO: 63) | Fc fragment of IgG binding protein |
| FCN1 | 2219 | GNHQFAKYKSFKVADE (SEQ ID NO: 64) | ficolin 1 precursor |
| FTL | 2512 | VSHFFRELAEEKREG (SEQ ID NO: 65) | ferritin, light polypeptide |
| FTL | 2512 | TPDAMKAAMALEKK (SEQ ID NO: 66) | ferritin, light polypeptide |
| GAPD | 2597 | FVMGVNHEKYDN (SEQ ID NO: 67) | glyceraldehyde-3-phosphate dehydrogenase |
| GAPD | 2597 | TGVFTTMEKAGAH (SEQ ID NO: 68) | glyceraldehyde-3-phosphate dehydrogenase |
| GAPD | 2597 | ISWYDNEFGYSNRVVDLMAHMASKE (SEQ ID NO: 69) | glyceraldehyde-3-phosphate dehydrogenase |
| HIST1H1C | 3006 | GTGASGSFKLNKKAASGEAKPK (SEQ ID NO: 70) | H1 histone family, member 2 |
| HLA-DQB1 | 3119 | DVGVYRAVTPQGRPD (SEQ ID NO: 71) | major histocompatibility complex, class II, DQ beta 1 precursor |
| HLA-DRB1 | 3123 | DVGEFRAVTELGRPD (SEQ ID NO: 72) | major histocompatibility complex, class II, DR beta 1 precursor |
| IGFBP3 | 3486 | HPLHSKIIIIKKGHAK (SEQ ID NO: 73) | insulin-like growth factor binding protein 3 |

TABLE 3-continued

Example list of HLA-DR ligands isolated from RCC190.
Shown are the core sequences of HLA-DR ligands isolated from
RCC190 (HLA-DRB1*11, DRB1*15, DRB3, DRB5).

| Gene Symbol | Entrez GeneID | Peptide Sequence (SEQ ID NO:) | Gene Title |
|---|---|---|---|
| KNG1 | 3827 | DKDLFKAVDAALKK (SEQ ID NO: 74) | kininogen 1 |
| NPC2 | 10577 | KDKTYSYLNKLPVK (SEQ ID NO: 75) | Niemann-Pick disease, type C2 precursor |
| S100A8 | 6279 | VIKMGVAAHKKSHEESHKE (SEQ ID NO: 76) | S100 calcium-binding protein A8 |
| SERPINA1 | 5265 | MIEQNTKSPLFMGKVVNPTQK (SEQ ID NO: 77) | serine (or cysteine) proteinase inhibitor, clade A (alpha-1 antiproteinase, antitrypsin), member 1 |
| SOD1 | 6647 | GPHFNPLSRKHGGPK (SEQ ID NO: 78) | superoxide dismutase 1, soluble |
| TF | 7018 | DPQTFYYAVAVVKKDS (SEQ ID NO: 79) | transferrin |

There was no correlation between tumor weight and number of identified HLA ligands. Peptide source proteins could be divided into two groups. On the one hand, ligands which should be presented by leukocytes were found, such as peptides from complement components, e.g., C3, C4A, C4 binding protein alpha, and other proteins linked to specific functions of cells of the immune system, e.g., CD14, and Fc fragment of IgG binding protein. On the other hand, the inventors were able to disclose the nature and characteristics of previously unknown peptides presented by tumor cells from over-expressed TAA, for example from vimentin, matrix metalloproteinase 7, eukaryotic translation elongation factor 1 alpha 1, and nicotinamide N-methyltransferase. This observation is in accordance with immuno-histochemistry data (FIGS. 1 and 4) and demonstrates that HLA class II positive tumor cells and infiltrating leukocytes were present in analyzed specimens and that the eluted peptides stem from antigens found to be over-expressed in these distinct cell types.

To identify peptides from TAA, the inventors compared the source proteins for the individual ligands with over-expressed genes detected by micro-array analysis of tumors (Weinschenk, T., C. Gouttefangeas, M. Schirle, F. Obermayr, S. Walter, O. Schoor, R. Kurek, W. Loeser, K. H. Bichler, D. Wernet, S. Stevanovic, and H. G. Rammensee. 2002. Integrated functional genomics approach for the design of patient-individual antitumor vaccines. Cancer Res. 62:5818-5827; Krüger, T., O. Schoor, C. Lemmel, B. Kraemer, C. Reichle, J. Dengjel, T. Weinschenk, M. Müller, J. Hennenlotter, A. Stenzl, H. G. Rammensee, and S. Stevanovic. 2004. Lessons to be learned from primary renal cell carcinomas: novel tumor antigens and HLA ligands for immunotherapy. Cancer Immunol. Immunother). The inventors identified a peptide from insulin-like growth factor binding protein 3, IGFBP3$_{166-181}$, on RCC190. In addition, two variants of this peptide, IGFBP3$_{169-181}$ and IGFBP3$_{169-184}$, which contain the same sequence core motif that is both necessary and sufficient to allow binding to HLA-DRB1*0101 (for reference, see Table 1), were found on TCC108. From the same tumor, a peptide from matrix metalloproteinase 7, MMP7$_{247-262}$, could be isolated (Table 1). At the mRNA level, MMP7 was over-expressed in 13 and IGFBP3 in 22 of 23 analyzed RCC (data not shown). In total, out of 453 peptide sequences initially identified (not shown), the underlying antigens for 49 peptides (SEQ ID NOS: 1-49) have been identified to be tumor-associated, either by the experiments of the inventors (data included in this document), or by others (Miyamoto, S., K. Yano, S. Sugimoto, G. Ishii, T. Hasebe, Y. Endoh, K. Kodama, M. Goya, T. Chiba, and A. Ochiai. 2004. Matrix metalloproteinase-7 facilitates insulin-like growth factor bioavailability through its proteinase activity on insulin-like growth factor binding protein 3. Cancer Res. 64:665-671; Sumi, T., T. Nakatani, H. Yoshida, Y. Hyun, T. Yasui, Y. Matsumoto, E. Nakagawa, K. Sugimura, H. Kawashima, and O. Ishiko. 2003. Expression of matrix metalloproteinases 7 and 2 in human renal cell carcinoma. Oncol. Rep. 10:567-570; Cheung, C. W., D. A. Vesey, D. L. Nicol, and D. W. Johnson. 2004. The roles of IGF-I and IGFBP-3 in the regulation of proximal tubule, and renal cell carcinoma cell proliferation. Kidney Int. 65:1272-1279; Hao, X., B. Sun, L. Hu, H. Lahdesmaki, V. Dunmire, Y. Feng, S. W. Zhang, H. Wang, C. Wu, H. Wang, G. N. Fuller, W. F. Symmans, I. Shmulevich, and W. Zhang. 2004. Differential gene and protein expression in primary breast malignancies and their lymph node metastases as revealed by combined cDNA microarray and tissue microarray analysis. Cancer 100:1110-1122; Helmke, B. M., M. Polychronidis, A. Benner, M. Thome, J. Arribas, and M. Deichmann. 2004. Melanoma metastasis is associated with enhanced expression of the syntenin gene. Oncol. Rep. 12:221-228; Hofmann, H. S., G. Hansen, G. Richter, C. Taege, A. Simm, R. E. Silber, and S. Burdach. 2005. Matrix metalloproteinase-12 expression correlates with local recurrence and metastatic disease in non-small cell lung cancer patients. Clin. Cancer Res. 11: 1086-1092; Kamai, T., T. Yamanishi, H. Shirataki, K. Takagi, H. Asami, Y. Ito, and K. Yoshida. 2004. Overexpression of RhoA, Rac1, and Cdc42 GTPases is associated with progression in testicular cancer. Clin. Cancer Res. 10:4799-4805; Koninger, J., N. A. Giese, F. F. di Mola, P. Berberat, T. Giese, I. Esposito, M. G. Bachem, M. W. Buchler, and H. Friess. 2004. Overexpressed decorin in pancreatic cancer: potential tumor growth inhibition and attenuation of chemotherapeutic action. Clin. Cancer Res. 10:4776-4783; Mori, M., H. Shimada, Y. Gunji, H. Matsubara, H. Hayashi, Y. Nimura, M. Kato, M. Takiguchi, T. Ochiai, and N. Seki. 2004. S100A11 gene identified by in-house cDNA microarray as an accurate predictor of lymph node metastases of gastric cancer. *Oncol. Rep.* 11:1287-1293; Nagler, D. K., S. Kruger, A. Kellner, E. Ziomek, R. Menard, P. Buhtz, M. Krams, A. Roessner, and U. Kellner. 2004. Up-regulation of cathepsin X in prostate cancer and prostatic intraepithelial neoplasia. *Prostate* 60:109-119; Nanda, A., P. Buckhaults, S. Seaman, N. Agrawal, P. Boutin, S. Shankara, M. Nacht, B. Teicher, J. Stampfl, S. Singh, B. Vogelstein, K. W. Kinzler, and C. B. St. 2004. Identification of a binding partner for the endothelial cell surface proteins TEM7 and TEM7R. *Cancer Res.* 64:8507-8511; Patel, I. S., P. Madan, S. Getsios, M. A. Bertrand, and C. D. MacCalman. 2003. Cadherin switching in ovarian cancer progression. *Int. J. Cancer* 106:172-177; Santelli, G., D. Califano, G. Chiappetta, M. T. Vento, P. C. Bartoli, F. Zullo, F. Trapasso, G. Viglietto, and A. Fusco. 1999. Thymosin beta-10 gene overexpression is a general event in human carcinogenesis. *Am. J. Pathol.* 155:799-804; Schneider, D., J. Kleeff, P. O. Berberat, Z. Zhu, M. Korc, H. Friess, and M. W. Buchler. 2002. Induction and expression of betaig-h3 in pancreatic cancer cells. *Biochim. Biophys. Acta* 1588:1-6; Welsh, J. B., L. M. Sapinoso, S. G. Kern, D. A. Brown, T. Liu, A. R. Bauskin, R. L. Ward, N. J. Hawkins, D. I. Quinn, P. J. Russell, R. L. Sutherland, S. N. Breit, C. A. Moskaluk, H. F. Frierson, Jr., and G. M. Hampton. 2003. Large-scale delineation of secreted protein biomarkers overexpressed in cancer tissue and serum. *Proc. Natl. Acad. Sci. U.S.A* 100:3410-3415; Xie, D., J. S. Sham, W. F. Zeng, L. H. Che, M. Zhang, H. X. Wu, H. L. Lin, J. M. Wen, S. H. Lau, L. Hu, and X. Y. Guan. 2005. Oncogenic role of clusterin overexpression in multistage colorectal tumorigenesis and progression. *World J. Gastroenterol.* 11:3285-3289). Exemplary analysis of immuno-stimulatory potential of peptides binding to common HLA-DR alleles reveals the existence of antigen-specific CD4-positive T-cells against IGFBP3$_{169-181}$ and MMP7$_{247-262}$.

Promiscuous binding of exemplary SEQ ID NO: 1 to several HLA-DR alleles can be revealed by several independent methods: ligands of certain MHC/HLA molecules carry chemical related amino acids in certain positions of their primary sequence, which permit the definition of a peptide motif for every MHC/HLA allele (Falk K, Rotzschke O, Stevanovic S, Jung G, Rammensee H G. Allele-specific motifs revealed by sequencing of self-peptides eluted from MHC molecules. Nature. 1991; 351(6324):290-6). SYFPEITHI uses motif matrices deduced from refined motifs exclusively based on natural ligand analysis by Edman degradation and tandem mass spectrometry. These matrices allow the prediction of peptides from a given protein sequence presented on MHC class I or class II molecules (Rotzschke O, Falk K, Stevanovic S, Jung G, Walden P, Rammensee H G. Exact prediction of a natural T-cell epitope. Eur J. Immunol. 1991; 21(11):2891-4).

Applying the principles of the predictions made by the SYFPEITHI algorithm (Rammensee, H. G., J. Bachmann, and S. Stevanovic. 1997. MHC Ligands and Peptide Motifs. Springer-Verlag, Heidelberg, Germany; Rammensee H, Bachmann J, Emmerich N P, Bachor O A, Stevanovic S. SYFPEITHI: database for MHC ligands and peptide motifs. Immunogenetics. 1999; 50(3-4):213-9) to the aforesaid exemplary peptide sequence (SEQ ID NO: 1), the binding of SEQ ID NO: 1 to several common HLA-DR alleles (see Table 7) was ranked. The algorithm has been successfully used to predict class I and class II epitopes from various antigens, e.g., from the human TAA TRP2 (prediction of an HLA class I ligand) (34) and SSX2 (prediction of an HLA class II ligand) (Neumann F, Wagner C, Stevanovic S, Kubuschok B, Schormann C, Mischo A, Ertan K, Schmidt W, Pfreundschuh M. Identification of an HLA-DR-restricted peptide epitope with a promiscuous binding pattern derived from the cancer testis antigen HOM-MEL-40/SSX2. Int J. Cancer. 2004; 112(4):661-8). The threshold of a score of 18 or higher for significant binding was defined based on the analysis of binding scores for previously published promiscuously binding HLA-DR peptide ligands. Promiscuous binding is defined as binding of a peptide with good binding strength as indicated by a score of 18 in the SYFPEITHI test or higher to two or more different common HLA-DR alleles. The most common HLA DR alleles are depicted in Table 7. The loci of HLA-A and HLA-DR are in linkage disequilibrium yielding combinations of HLA-A2 and specific HLA-DRs that are favored in comparison to others. The HLA-DR genotypes of the source tumors were analyzed and confirmed to be HLA-DRB 1*11 and DRB1*15 in both cases. The preferred anchor amino acid residues for the most common HLA class II alleles (DRB1*0101, DRB1*0301, DRB1*0401, DRB1*0701, DRB1*1101, and DRB1*1501) are depicted in Table 4. For example, the HLA class II allele DRB1*0301 preferentially binds peptides in its binding groove that feature specific amino acid residues in positions 1, 4, 6, and 9 from the N- to the C-terminal end of the core sequence of any given peptide. Specifically, DRB1*0301 shows good binding, if the core sequence of a peptide has a Glutamate residue (D) in position 4, as well as either L, I, F, M, or V in position 1, as well as K, R, E, Q, or N in position 6, as well as either Y, L, or F in position 9.

TABLE 4

Peptide motifs of common HLA-DR alleles. Depicted are anchor amino acids in one letter code at the corresponding binding pockets.

| HLA allel | -3 | -2 | -1 | 1 | 2 | 3 | 4 | 5 | 6 | 7 | 8 | 9 | +1 | +2 | +3 |
|---|---|---|---|---|---|---|---|---|---|---|---|---|---|---|---|
| DRB1*0101 |  |  |  | Y |  |  | L |  | A |  |  | L |  |  |  |
|  |  |  |  | V |  |  | A |  | G |  |  | I |  |  |  |
|  |  |  |  | L |  |  | I |  | S |  |  | A |  |  |  |
|  |  |  |  | I |  |  | V |  | T |  |  | V |  |  |  |
|  |  |  |  | F |  |  | M |  | C |  |  | N |  |  |  |
|  |  |  |  | A |  |  | N |  | P |  |  | F |  |  |  |
|  |  |  |  | M |  |  | Q |  |   |  |  | Y |  |  |  |
|  |  |  |  | W |  |  |   |  |   |  |  |   |  |  |  |
| DRB1*0301 |  |  |  | L |  |  | D |  | K |  |  | Y |  |  |  |
|  |  |  |  | I |  |  |   |  | R |  |  | L |  |  |  |
|  |  |  |  | F |  |  |   |  | E |  |  | F |  |  |  |
|  |  |  |  | M |  |  |   |  | Q |  |  |   |  |  |  |
|  |  |  |  | V |  |  |   |  | N |  |  |   |  |  |  |
| DRB1*0401 |  |  |  | F |  |  | P |  | N |  |  | D | D |  |  |
|  |  |  |  | Y |  |  | W |  | S |  |  | E | E |  |  |
|  |  |  |  | W |  |  | I |  | T |  |  | H | H |  |  |
|  |  |  |  | I |  |  | L |  | Q |  |  | K | K |  |  |
|  |  |  |  | L |  |  | V |  | H |  |  | N | N |  |  |
|  |  |  |  | V |  |  | A |  | R |  |  | Q | Q |  |  |
|  |  |  |  | M |  |  | D |  |   |  |  | R | R |  |  |
|  |  |  |  |   |  |  | E |  |   |  |  | S | S |  |  |
|  |  |  |  |   |  |  |   |  |   |  |  | T | T |  |  |
|  |  |  |  |   |  |  |   |  |   |  |  | Y | Y |  |  |
|  |  |  |  |   |  |  |   |  |   |  |  | A | A |  |  |
|  |  |  |  |   |  |  |   |  |   |  |  | C | C |  |  |
|  |  |  |  |   |  |  |   |  |   |  |  | I | I |  |  |
|  |  |  |  |   |  |  |   |  |   |  |  | L | L |  |  |
|  |  |  |  |   |  |  |   |  |   |  |  | M | M |  |  |
|  |  |  |  |   |  |  |   |  |   |  |  | V | V |  |  |
| DRB1*0701 |  |  |  | F |  |  | D |  | N |  |  | V |  |  |  |
|  |  |  |  | Y |  |  | E |  | S |  |  | I |  |  |  |
|  |  |  |  | W |  |  | H |  | T |  |  | L |  |  |  |
|  |  |  |  | I |  |  | K |  |   |  |  | Y |  |  |  |
|  |  |  |  | L |  |  | N |  |   |  |  | F |  |  |  |
|  |  |  |  | V |  |  | Q |  |   |  |  |   |  |  |  |
|  |  |  |  |   |  |  | R |  |   |  |  |   |  |  |  |
|  |  |  |  |   |  |  | S |  |   |  |  |   |  |  |  |

TABLE 4-continued

Peptide motifs of common HLA-DR alleles. Depicted are anchor amino acids in one letter code at the corresponding binding pockets.

| HLA allel | -3 | -2 | -1 | 1 | 2 | 3 | 4 | 5 | 6 | 7 | 8 | 9 | +1 | +2 | +3 |
|---|---|---|---|---|---|---|---|---|---|---|---|---|---|---|---|
|  |  |  |  |  |  | T |  |  |  |  |  |  |  |  |  |
|  |  |  |  |  |  | Y |  |  |  |  |  |  |  |  |  |
| DRB1*1101 |  |  |  | W |  |  | L |  | R |  |  | A |  |  |  |
|  |  |  |  | Y |  |  | I |  | K |  |  | G |  |  |  |
|  |  |  |  | F |  |  | V |  | H |  |  | S |  |  |  |
|  |  |  |  |  |  |  | M |  |  |  |  | P |  |  |  |
|  |  |  |  |  |  |  | A |  |  |  |  |  |  |  |  |
|  |  |  |  |  |  |  | F |  |  |  |  |  |  |  |  |
|  |  |  |  |  |  |  | Y |  |  |  |  |  |  |  |  |
| DRB1*1501 |  |  |  | L |  |  | F |  | I |  |  |  |  |  |  |
|  |  |  |  | V |  |  | Y |  | L |  |  |  |  |  |  |
|  |  |  |  | I |  |  | I |  | V |  |  |  |  |  |  |
|  |  |  |  |  |  |  |  |  | M |  |  |  |  |  |  |
|  |  |  |  |  |  |  |  |  | F |  |  |  |  |  |  |

Results from in silico analysis based on the computer algorithms for the prediction of interaction between HLA molecules and peptide sequences provided through www.syfpeithi.de indicate that the peptide MMP7$_{247-262}$ SEQ ID NO: 1 binds promiscuously to several HLA-DR alleles. According to results from the predictive analysis, the peptide with SEQ ID NO: 1 receives a high binding score for interaction with DRB1*1101, DRB1*1501, DRB1*0401, DRB1*0301, and DRB1*0101 (Table 7). The HLA-DR alleles analyzed in this test for interaction with the peptide amino acid sequence/strength of binding cover at least 69.6% of the HLA-A2 positive Caucasian population (Mori M, Beatty P G, Graves M, Boucher K M, Milford E L. HLA gene and haplotype frequencies in the North American population: the National Marrow Donor Program Donor Registry. Transplantation. 1997; 64(7):1017-27). As there is presently no frequency data available for HLA-DR15, the allele was not taken into consideration for calculating the resulting coverage of the HLA-A2 positive Caucasian population. Thus, it is very likely that with SEQ ID NO: 1, the coverage of the population is even higher than 69.6%, which indicates that the peptide has an excellent perspective for serving as a candidate for the development of pharmaceutical preparations for the majority of cancer patients.

However, application of prediction algorithms leads only to conclusive results, if the results from in silico analyses are combined with experimental confirmation for promiscuous binding, as was shown by others before, who failed to demonstrate any immune responses triggered by a peptide sequences predicted to be a good binder (Bohm C M, Hanski M L, Stefanovic S, Rammensee H G, Stein H, Taylor-Papadimitriou J, Riecken E O. Hanski C. Identification of HLA-A2-restricted epitopes of the tumor-associated antigen MUC2 recognized by human cytotoxic T-cells. Int J. Cancer. 1998; 75(5):688-93). The prediction of artifacts like in the afore-mentioned case can principally not be ruled out, as the algorithms used for prediction do not take into account that a peptide sequence is not necessarily generated in an in vivo situation (inside living cells). Experimental confirmation can be obtained by collecting in vitro data from biological test, e.g., by demonstrating the presence or lack of immunogenicity of a peptide. Hence, for experimental confirmation of promiscuous binding of SEQ ID NO: 1 was obtained by collecting such in vitro data. To test the peptides for their immuno-stimulatory capacity by in vitro T-cell priming experiments, the shortest variants ("core sequence") of the IGFBP3 peptides, IGFBP3$_{169-181}$, and of the MMP7 peptide, MMP7$_{247-262}$, were used.

To generate antigen-specific CD4-positive T-cells and to test the peptides for promiscuous binding, PBMCs of 4 healthy donors with different HLA-DR alleles (FIG. 2), one of them carrying DRB1*1101, were stimulated using peptide-pulsed autologous DCs. In addition, the peptide CCND1$_{198-212}$, a known T-cell epitope (Dengjel, J., P. Decker, O. Schoor, F. Altenberend, T. Weinschenk, H. G. Rammensee, and S. Stevanovic. 2004. Identification of a naturally processed cyclin D1 T-helper epitope by a novel combination of HLA class II targeting and differential mass spectrometry. Eur. J. Immunol. 34:3644-3651), was used as positive control. As a read-out system for the generation of antigen-specific CD4-positive T-cells, IFNγ levels were assessed by flow cytometry. T-cells were analyzed after the third and fourth weekly stimulation by intracellular IFNγ staining plus CD4-FITC and CD8-PerCP staining to determine the percentage of IFNγ-producing cells in specific T-cell subpopulations. In all experiments, stimulations with irrelevant peptide and without peptide were performed as negative controls. IFNγ response was considered as positive if the percentage of IFNγ producing CD4-positive T-cells was more than two-fold higher compared with negative controls (Horton, H., N. Russell, E. Moore, I. Frank, R. Baydo, C. Havenar-Daughton, D. Lee, M. Deers, M. Hudgens, K. Weinhold, and M. J. Mc Elrath. 2004. Correlation between interferon-gamma secretion and cytotoxicity, in virus-specific memory T-cells. J. Infect. Dis. 190:1692-1696).

Figure 2A:
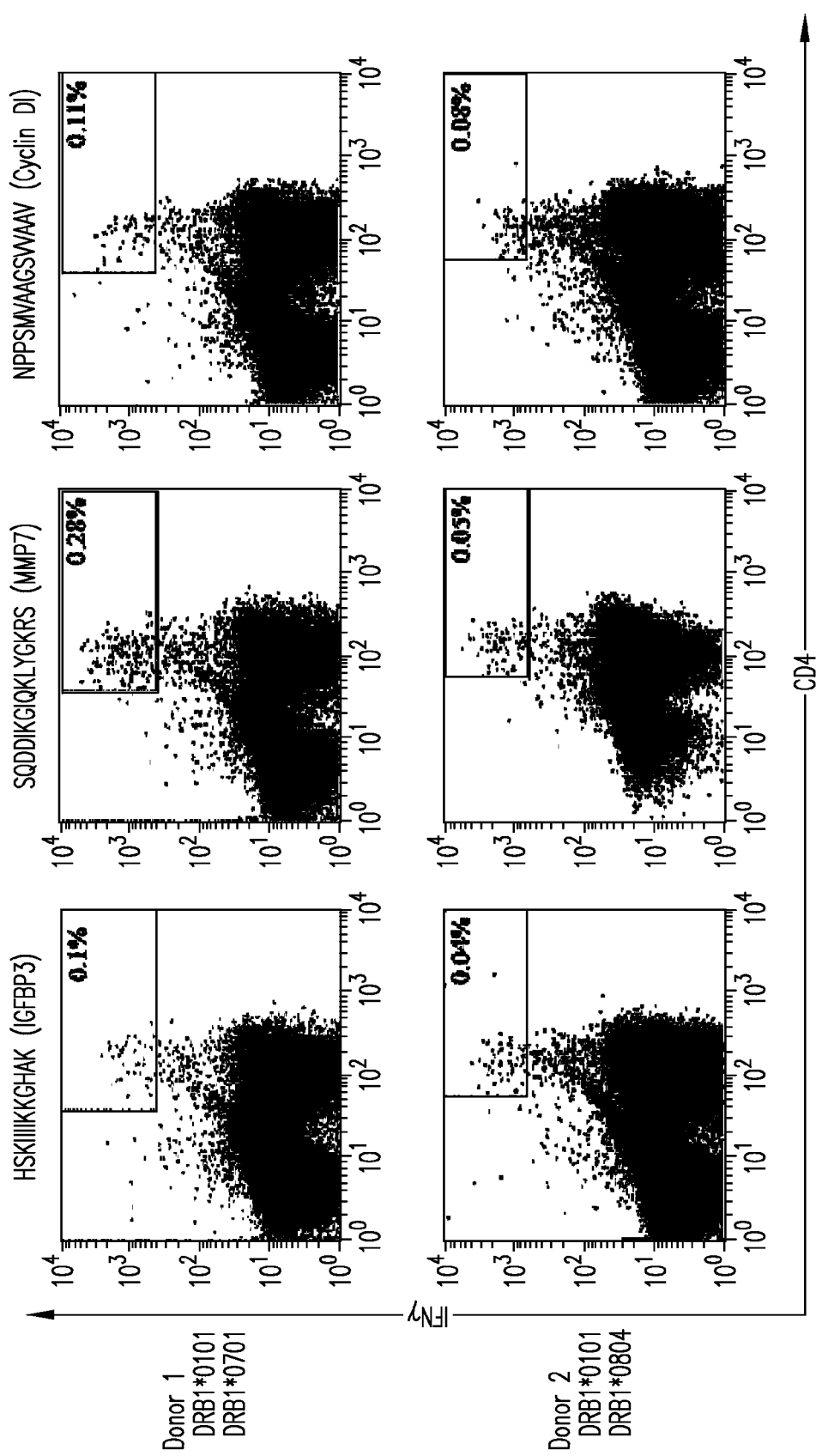
FIG. 2 shows a FACS analysis of CD4-positive T-cells specific for $IGFBP3_{169-181}$, $MMP7_{247-262}$ and $CCND1_{198-212}$. Shown are representative dot blots of intracellular IFNγ staining against CD4-FITC.
Figure 2B:
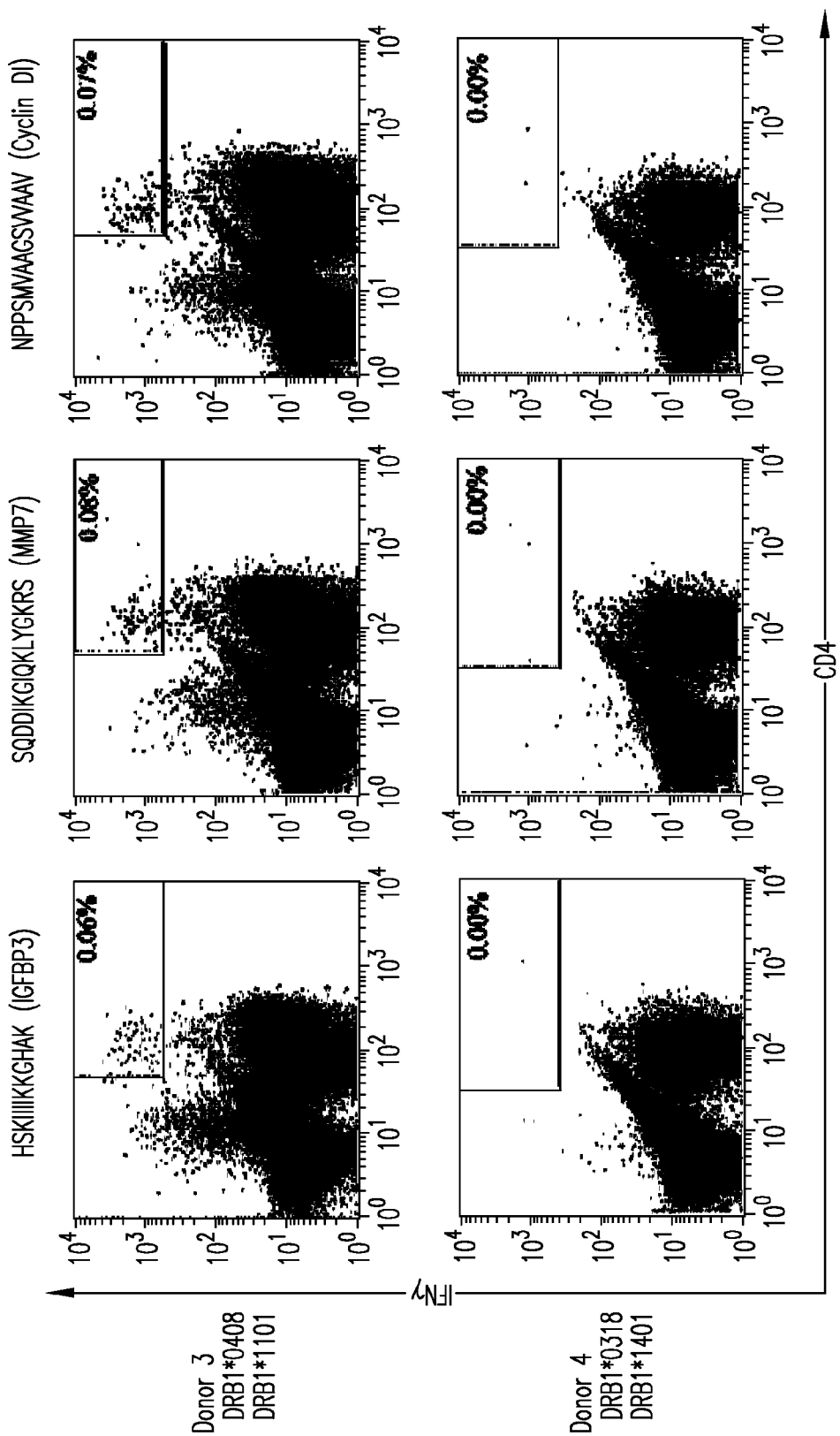
Figure 3A:
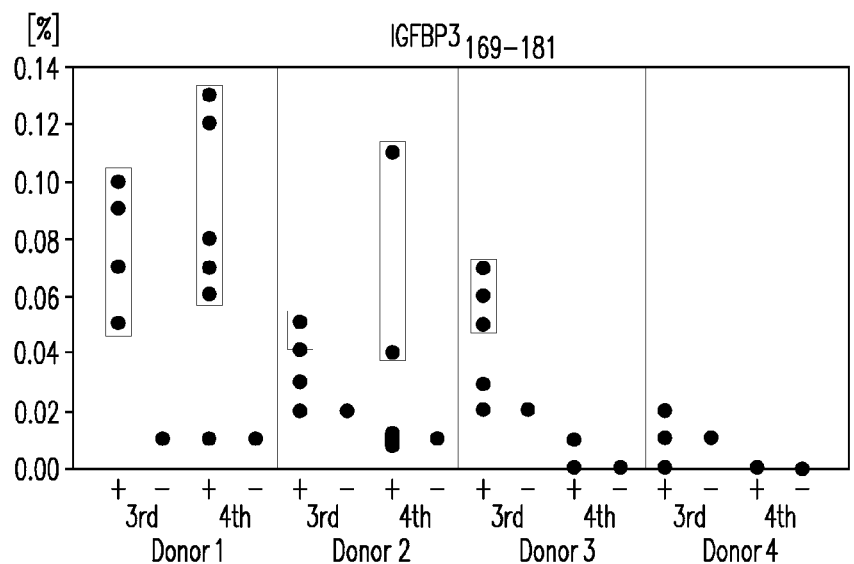
FIG. 3 shows a schematic illustration of antigen-specific IFNγ producing CD4-positive T-cells detected in each donor and for each peptide. Shown is the percentage of IFNγ producing CD4-positive T-cells for each donor and peptide used for stimulation. Cells were incubated in 96-well plates—7 wells per donor and per peptide. Boxed are values considered as positive: percentage of IFNγ producing CD4-positive T-cells was more than two-fold higher compared with negative control without peptide. Percentages of IFNγ producing CD4-positive T-cells detected after stimulation with irrelevant peptide correlated with values after stimulation without peptide, with the exception of Donor 1 after the $3^{rd}$ stimulation with $IGFBP3_{169-181}$. However, this effect was not seen anymore after the $4^{th}$ stimulation.
Figure 3B:
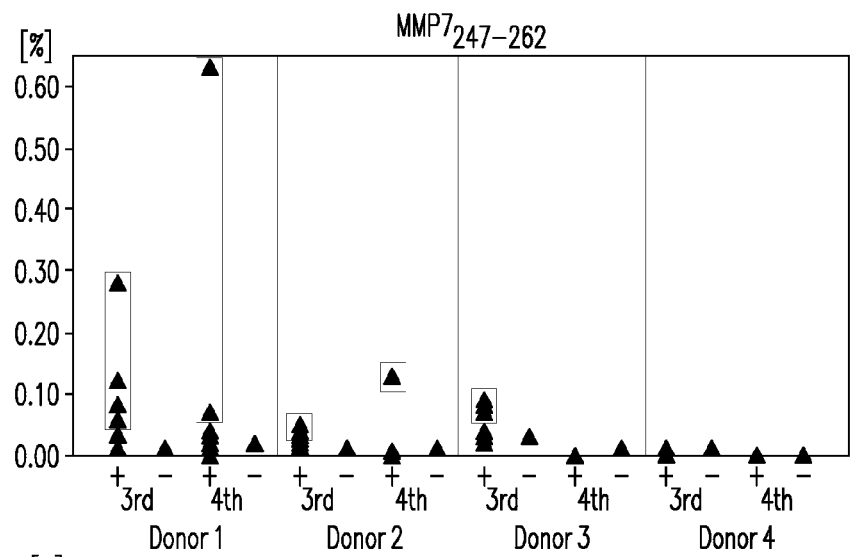
Figure 3C:
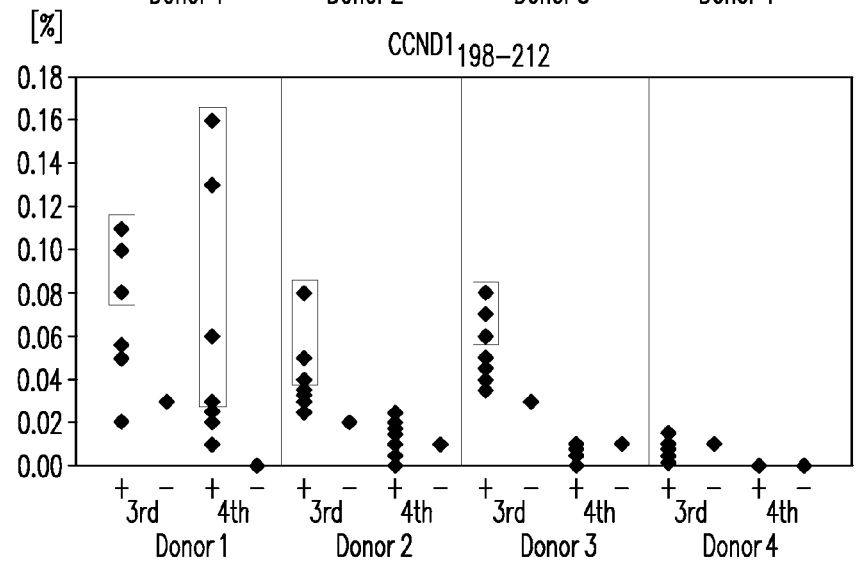
Figure 4A:
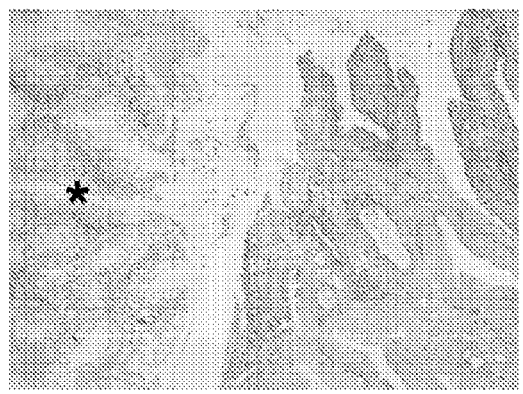
FIG. 4 shows the expression of HLA class II molecules in CCA165 (moderately differentiated adenocarcinoma of the colon). In the lamina propria of areas with normal colonic mucosa (panel c and left side of panel a, marked by asterisk) typically some HLA class II positive macrophages are observed but epithelial cells were consistently negative for HLA class II expression. In epithelial cells from different areas of the tumor, however, a pronounced expression of HLA II was noted as shown on the right side of panel a, and in panel b and d.
Figure 4B:
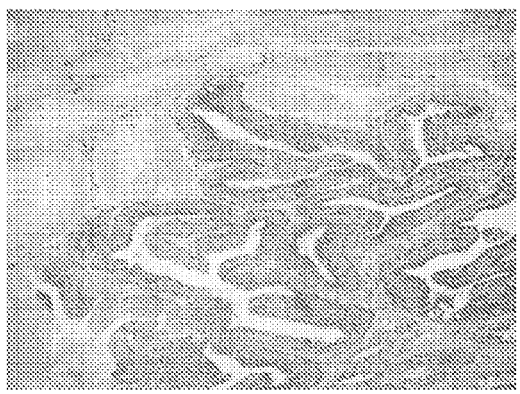
Figure 4C:
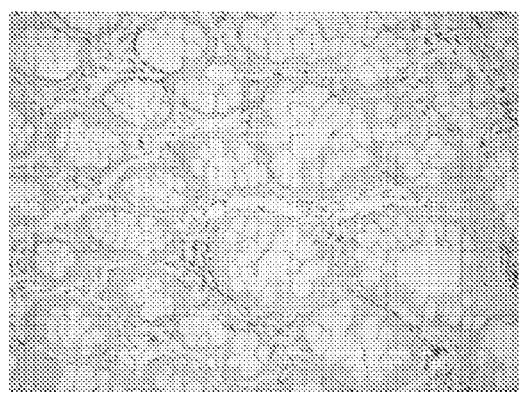
Figure 4D:
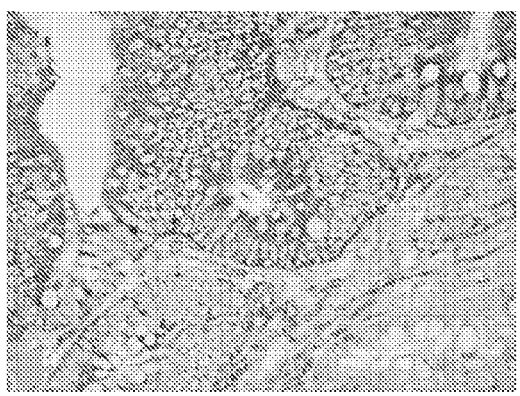

In three of four donors the inventors were able to generate specific CD4-positive T-cells for both peptides (FIG. 2). T-cell responses could not be observed in donor 4 after any stimulation. In donor 1, 0.05% to 0.1% (FIG. 3) IFNγ producing CD4-positive T-cells were detected in all seven stimulation attempts after the third stimulation with peptide IGFBP3$_{169-181}$. These T-cells could be expanded in most cases by an additional round of stimulation to 0.09% to 0.13%. IFNγ-producing CD4-positive T-cells specific for the peptide IGFBP3$_{169-181}$ were also observed in donor 2 and donor 3, with maximal frequencies of 0.05% and 0.07% IFNγ producing CD4$^+$ T-cells.

Donors 1, 2, and 3 also showed CD4$^+$ T-cells reactive to peptide MMP7$_{247-262}$. The highest frequencies of IFNγ producing CD4$^+$ T-cells specific for the MMP7 peptide were found in donors 1 and 2, respectively. Donors 1, 2, and 3 showed IFNγ responses to peptide CCND1$_{198-212}$, which had already been described as an MHC class II-restricted T-cell epitope (Dengjel, J., P. Decker, O. Schoor, F. Altenberend, T. Weinschenk, H. G. Rammensee, and S. Stevanovic. 2004. Identification of a naturally processed cyclin D1 T-helper epitope by a novel combination of HLA class II targeting and differential mass spectrometry. Eur. J. Immunol. 34:3644-3651).

Thus, peptides from IGFBP3, MMP7, and CCND1 are promiscuous HLA class II binders that are able to elicit CD4-positive T-cell responses in three out of four healthy donors carrying different HLA DR alleles. If the HLA alleles of the two tumour patients from which the IGFBP3 and MMP7 peptides were derived are compared to those of the four healthy donors, it becomes obvious that the peptides are presented by HLA-DRB1*01, HLA-DRB1*04 and HLA-DRB1*11. All three aforesaid HLA DR allotypes have a glycine amino acid residue at position 86, and an aspartic acid residue at position 57 of their β chains, respectively (see www.anthonynolan.com/HIG). Therefore, they have very similar binding characteristics for their binding pockets P1 and P9 (Rammensee, H. G., J. Bachmann, and S. Stevanovic. 1997. MHC Ligands and Peptide Motifs. Springer-Verlag, Heidelberg, Germany). For peptide CCND1$_{198-212}$, a T-cell epitope known to be presented by HLA-DRB1*0401 and HLA-DRB1*0408 (Dengjel, J., P. Decker, O. Schoor, F. Altenberend, T. Weinschenk, H. G. Rammensee, and S. Stevanovic. 2004. Identification of a naturally processed cyclin D1 T-helper epitope by a novel combination of HLA class II targeting and differential mass spectrometry. *Eur. J. Immunol.* 34:3644-3651), the same holds true. Donor 4 carries HLA-DRB1*0318 and HLA-DRB1*1401, alleles with peptide motifs that differ in the primary amino acid sequence of their beta chains from those described above. This could explain why it was not possible to elicit T-cell responses against the two peptides using cells from this donor.

Interestingly, IFNγ-producing CD8-positive killer T-cells were detected in two donors after stimulations with the three peptides, in particular in donor 3, but also to a lesser extent in donor 1 (data not shown).

TABLE 5

| Fragment | Mass [M + H]+ | Amino acid sequence |
|---|---|---|
| b2 | 216.1 | SQ |
| y4 | 447.3 | GKRS |
| y6 | 723.4 | LYGKRS |
| y7 | 851.5 | KLYGKRS |
| y8 | 979.6 | QKLYGKRS |
| y9 | 1092.6 | IQKLYGKRS |
| y10 | 1149.7 | GIQKLYGKRS |
| y11 | 1277.8 | KGIQKLYGKRS |
| y12 | 1390.8 | IKGIQKLYGKRS |
| y13 | 1505.9 | DIKGIQKLYGKRS |
| y14 | 1620.9 | DDIKGIQKLYGKRS |
| R | 129.1 | immonium R |

TABLE 6

Table 6: Haplotype frequencies of North American Caucasian population. Shown are the serological haplotypes.

| Haplotype | | Frequency |
|---|---|---|
| HLA-A | HLA-DR | [%] |
| 2 | 1 | 8.8 |
| 2 | 2 | 14.9 |
| 2 | 3 | 6.1 |
| 2 | 4 | 21.3 |
| 2 | 5 | 1.2 |
| 2 | 6 | 15.2 |
| 2 | 7 | 13.0 |
| 2 | 8 | 4.2 |
| 2 | 9 | 1.2 |
| 2 | 10 | 1.4 |
| 2 | 11 | 8.7 |
| 2 | 12 | 2.6 |
| 2 | n.a. | 1.4 |

"n.a." stands for not assigned.

TABLE 7

Binding scores of SEQ ID NO: 1 to common HLA-DR alleles Shown are the SEQ ID NO: 1 and SEQ ID NO: 25 SYFPEITHI binding scores for the most common HLA-DRB1 alleles in Caucasian populations. The frequencies of the corresponding serological haplotypes of HLA-A2 positive Caucasians are given in brackets. The peptides are considered to bind sufficiently well to a HLA class II molecule, if the score was equal to- or higher than 18.

| Antigen | DRB1* allele | | | | | |
|---|---|---|---|---|---|---|
| | 0101 (8.8%) | 0301 (6.1%) | 0401 (21.3%) | 0701 (13.0%) | 1101 (8.7%) | 1501 (n.a. %) |
| SEQ ID NO: 1 | 35 | 18 | 20 | 14 | 26 | 20 |
| SEQ ID NO: 25 | 28 | 28 | 20 | 18 | 26 | 18 |

---

I claim:

1. An isolated tumour associated peptide consisting of the peptide set forth in SEQ ID NO: 4 flanked by N- and/or C-terminal extensions from 1 to 10 amino acids in length.

2. The isolated tumour associated peptide according to claim 1 wherein said isolated tumor associated peptide has the ability to bind human major histocompatibility complex (MHC) class-II molecule HLA-DRB*0101, and has the ability to bind to at least one additional molecule of the human major histocompatibility complex (MHC) class-II.

3. A fusion protein comprising a peptide set forth in SEQ ID NO: 4, and N-terminal amino acids of HLA-DR antigen-associated invariant chain (Ii).

4. A pharmaceutical composition comprising the tumour associated peptide of claim 1 and a pharmaceutically acceptable carrier.

5. A method of killing target cells in a patient wherein the target cells aberrantly express a polypeptide comprising the amino acid sequence set forth in SEQ ID NO: 4, the method comprising administering to the patient an effective amount of the peptide of claim 1, wherein the amount of said peptide is effective to provoke an anti-target cell immune response in said patient.

6. An in vitro method for producing activated cytotoxic T lymphocytes (CTL), the method comprising contacting in vitro CTL with antigen loaded human class II MHC molecules expressed on the surface of a suitable antigen-presenting cell for a period of time sufficient to activate said CTL in an antigen specific manner, wherein said antigen is the peptide of claim 1.

7. Activated cytotoxic T lymphocytes (CTL), produced by the method of claim 6, wherein the CTL selectively recognise a cell that aberrantly expresses a polypeptide comprising the amino acid sequence set forth in SEQ ID NO: 4.

8. A pharmaceutical composition comprising a fusion protein of claim 3 and a pharmaceutically acceptable carrier.

9. An isolated tumour associated peptide consisting of the peptide set forth in SEQ ID NO: 4.

* * * * *

SEQUENCE LISTING

<160> NUMBER OF SEQ ID NOS: 79

<210> SEQ ID NO 1
<211> LENGTH: 17
<212> TYPE: PRT
<213> ORGANISM: Homo sapiens

<400> SEQUENCE: 1

Asn Pro Gly Glu Tyr Arg Val Thr Ala His Ala Glu Gly Tyr Thr Pro
1               5                   10                  15

Ser

<210> SEQ ID NO 2
<211> LENGTH: 17
<212> TYPE: PRT
<213> ORGANISM: Homo sapiens

<400> SEQUENCE: 2

Asn Lys Gln Lys Pro Ile Thr Pro Glu Thr Ala Glu Lys Leu Ala Arg
1               5                   10                  15

-continued

Asp

<210> SEQ ID NO 3
<211> LENGTH: 16
<212> TYPE: PRT
<213> ORGANISM: Homo sapiens

<400> SEQUENCE: 3

Asp Asp Pro Ser Thr Ile Glu Lys Leu Ala Lys Asn Lys Gln Lys Pro
1               5                   10                  15

<210> SEQ ID NO 4
<211> LENGTH: 15
<212> TYPE: PRT
<213> ORGANISM: Homo sapiens

<400> SEQUENCE: 4

Asn Pro Leu Lys Ile Phe Pro Ser Lys Arg Ile Leu Arg Arg His
1               5                   10                  15

<210> SEQ ID NO 5
<211> LENGTH: 13
<212> TYPE: PRT
<213> ORGANISM: Homo sapiens

<400> SEQUENCE: 5

Glu Thr Gly Trp Leu Leu Leu Asn Lys Pro Leu Asp Arg
1               5                   10

<210> SEQ ID NO 6
<211> LENGTH: 13
<212> TYPE: PRT
<213> ORGANISM: Homo sapiens

<400> SEQUENCE: 6

Asp Asn Glu Leu Gln Glu Met Ser Asn Gln Gly Ser Lys
1               5                   10

<210> SEQ ID NO 7
<211> LENGTH: 15
<212> TYPE: PRT
<213> ORGANISM: Homo sapiens

<400> SEQUENCE: 7

Ala Ala Gly Leu Leu Ser Thr Tyr Arg Ala Phe Leu Ser Ser His
1               5                   10                  15

<210> SEQ ID NO 8
<211> LENGTH: 21
<212> TYPE: PRT
<213> ORGANISM: Homo sapiens

<400> SEQUENCE: 8

Ala Pro Ser Leu Arg Pro Lys Asp Tyr Glu Val Asp Ala Thr Leu Lys
1               5                   10                  15

Ser Leu Asn Asn Gln
            20

<210> SEQ ID NO 9
<211> LENGTH: 17
<212> TYPE: PRT
<213> ORGANISM: Homo sapiens

<400> SEQUENCE: 9

```
Gly Pro Val Asp Glu Val Arg Glu Leu Gln Lys Ala Ile Gly Ala Val
1               5                   10                  15

Pro

<210> SEQ ID NO 10
<211> LENGTH: 15
<212> TYPE: PRT
<213> ORGANISM: Homo sapiens

<400> SEQUENCE: 10

Ile Asn His Val Val Ser Val Ala Gly Trp Gly Ile Ser Asp Gly
1               5                   10                  15

<210> SEQ ID NO 11
<211> LENGTH: 18
<212> TYPE: PRT
<213> ORGANISM: Homo sapiens

<400> SEQUENCE: 11

Val Pro Asp Asp Arg Asp Phe Glu Pro Ser Leu Gly Pro Val Cys Pro
1               5                   10                  15

Phe Arg

<210> SEQ ID NO 12
<211> LENGTH: 20
<212> TYPE: PRT
<213> ORGANISM: Homo sapiens

<400> SEQUENCE: 12

Leu Pro Gln Ser Ile Val Tyr Lys Tyr Met Ser Ile Arg Ser Asp Arg
1               5                   10                  15

Ser Val Pro Ser
            20

<210> SEQ ID NO 13
<211> LENGTH: 16
<212> TYPE: PRT
<213> ORGANISM: Homo sapiens

<400> SEQUENCE: 13

Ile Val His Arg Tyr Met Thr Ile Thr Ser Glu Arg Ser Val Pro Ala
1               5                   10                  15

<210> SEQ ID NO 14
<211> LENGTH: 13
<212> TYPE: PRT
<213> ORGANISM: Homo sapiens

<400> SEQUENCE: 14

Lys Asn Gly Phe Val Val Leu Lys Gly Arg Pro Cys Lys
1               5                   10

<210> SEQ ID NO 15
<211> LENGTH: 15
<212> TYPE: PRT
<213> ORGANISM: Homo sapiens

<400> SEQUENCE: 15

Ile Thr Gly Tyr Ile Ile Lys Tyr Glu Lys Pro Gly Ser Pro Pro
1               5                   10                  15

<210> SEQ ID NO 16
```

```
<211> LENGTH: 14
<212> TYPE: PRT
<213> ORGANISM: Homo sapiens

<400> SEQUENCE: 16

Gly Ala Thr Tyr Asn Ile Ile Val Glu Ala Leu Lys Asp Gln
1               5                   10

<210> SEQ ID NO 17
<211> LENGTH: 16
<212> TYPE: PRT
<213> ORGANISM: Homo sapiens

<400> SEQUENCE: 17

Leu Thr Gly Tyr Arg Val Arg Val Thr Pro Lys Glu Lys Thr Gly Pro
1               5                   10                  15

<210> SEQ ID NO 18
<211> LENGTH: 16
<212> TYPE: PRT
<213> ORGANISM: Homo sapiens

<400> SEQUENCE: 18

Ile Pro Gly His Leu Asn Ser Tyr Thr Ile Lys Gly Leu Lys Pro Gly
1               5                   10                  15

<210> SEQ ID NO 19
<211> LENGTH: 12
<212> TYPE: PRT
<213> ORGANISM: Homo sapiens

<400> SEQUENCE: 19

Asn Leu Arg Phe Leu Ala Thr Thr Pro Asn Ser Leu
1               5                   10

<210> SEQ ID NO 20
<211> LENGTH: 17
<212> TYPE: PRT
<213> ORGANISM: Homo sapiens

<400> SEQUENCE: 20

Ser Asn Thr Asp Leu Val Pro Ala Pro Ala Val Arg Ile Leu Thr Pro
1               5                   10                  15

Glu

<210> SEQ ID NO 21
<211> LENGTH: 14
<212> TYPE: PRT
<213> ORGANISM: Homo sapiens

<400> SEQUENCE: 21

Ala Glu Ile Leu Glu Leu Ala Gly Asn Ala Ala Arg Asp Asn
1               5                   10

<210> SEQ ID NO 22
<211> LENGTH: 17
<212> TYPE: PRT
<213> ORGANISM: Homo sapiens

<400> SEQUENCE: 22

Val Lys Glu Pro Val Ala Val Leu Lys Ala Asn Arg Val Trp Gly Ala
1               5                   10                  15

Leu
```

```
<210> SEQ ID NO 23
<211> LENGTH: 16
<212> TYPE: PRT
<213> ORGANISM: Homo sapiens

<400> SEQUENCE: 23

Thr Ala Glu Ile Leu Glu Leu Ala Gly Asn Ala Ala Arg Asp Asn Lys
1               5                   10                  15

<210> SEQ ID NO 24
<211> LENGTH: 16
<212> TYPE: PRT
<213> ORGANISM: Homo sapiens

<400> SEQUENCE: 24

His Pro Leu His Ser Lys Ile Ile Ile Lys Lys Gly His Ala Lys
1               5                   10                  15

<210> SEQ ID NO 25
<211> LENGTH: 16
<212> TYPE: PRT
<213> ORGANISM: Homo sapiens

<400> SEQUENCE: 25

His Ser Lys Ile Ile Ile Ile Lys Lys Gly His Ala Lys Asp Ser Gln
1               5                   10                  15

<210> SEQ ID NO 26
<211> LENGTH: 18
<212> TYPE: PRT
<213> ORGANISM: Homo sapiens

<400> SEQUENCE: 26

Arg Pro Lys His Thr Arg Ile Ser Glu Leu Lys Ala Glu Ala Val Lys
1               5                   10                  15

Lys Asp

<210> SEQ ID NO 27
<211> LENGTH: 18
<212> TYPE: PRT
<213> ORGANISM: Homo sapiens

<400> SEQUENCE: 27

Gly Pro Glu Asp Asn Val Val Ile Ile Tyr Leu Ser Arg Ala Gly Asn
1               5                   10                  15

Pro Glu

<210> SEQ ID NO 28
<211> LENGTH: 16
<212> TYPE: PRT
<213> ORGANISM: Homo sapiens

<400> SEQUENCE: 28

Ser Arg Pro Val Ile Asn Ile Gln Lys Thr Ile Thr Val Thr Pro Asn
1               5                   10                  15

<210> SEQ ID NO 29
<211> LENGTH: 17
<212> TYPE: PRT
<213> ORGANISM: Homo sapiens

<400> SEQUENCE: 29

Leu Asp Leu Ser Phe Asn Gln Ile Ala Arg Leu Pro Ser Gly Leu Pro
```

-continued

```
1               5                   10                  15

Val

<210> SEQ ID NO 30
<211> LENGTH: 16
<212> TYPE: PRT
<213> ORGANISM: Homo sapiens

<400> SEQUENCE: 30

Lys Leu Pro Ser Val Glu Gly Leu His Ala Ile Val Val Ser Asp Arg
1               5                   10                  15

<210> SEQ ID NO 31
<211> LENGTH: 14
<212> TYPE: PRT
<213> ORGANISM: Homo sapiens

<400> SEQUENCE: 31

Asp Thr Ser Thr Leu Glu Met Met His Ala Pro Arg Cys Gly
1               5                   10

<210> SEQ ID NO 32
<211> LENGTH: 17
<212> TYPE: PRT
<213> ORGANISM: Homo sapiens

<400> SEQUENCE: 32

Asp Gln Asn Thr Ile Glu Thr Met Arg Lys Pro Arg Cys Gly Asn Pro
1               5                   10                  15

Asp

<210> SEQ ID NO 33
<211> LENGTH: 16
<212> TYPE: PRT
<213> ORGANISM: Homo sapiens

<400> SEQUENCE: 33

Ser Gln Asp Asp Ile Lys Gly Ile Gln Lys Leu Tyr Gly Lys Arg Ser
1               5                   10                  15

<210> SEQ ID NO 34
<211> LENGTH: 15
<212> TYPE: PRT
<213> ORGANISM: Homo sapiens

<400> SEQUENCE: 34

Leu Asp Phe Leu Lys Ala Val Asp Thr Asn Arg Ala Ser Val Gly
1               5                   10                  15

<210> SEQ ID NO 35
<211> LENGTH: 16
<212> TYPE: PRT
<213> ORGANISM: Homo sapiens

<400> SEQUENCE: 35

His Gly Asn Gln Ile Ala Thr Asn Gly Val Val His Val Ile Asp Arg
1               5                   10                  15

<210> SEQ ID NO 36
<211> LENGTH: 14
<212> TYPE: PRT
<213> ORGANISM: Homo sapiens

<400> SEQUENCE: 36
```

-continued

Arg Ala Ile Glu Ala Leu His Gly His Glu Leu Arg Pro Gly
1               5                   10

<210> SEQ ID NO 37
<211> LENGTH: 17
<212> TYPE: PRT
<213> ORGANISM: Homo sapiens

<400> SEQUENCE: 37

Asp Pro Gly Val Leu Asp Arg Met Met Lys Lys Leu Asp Thr Asn Ser
1               5                   10                  15

Asp

<210> SEQ ID NO 38
<211> LENGTH: 16
<212> TYPE: PRT
<213> ORGANISM: Homo sapiens

<400> SEQUENCE: 38

Asn Glu Glu Glu Ile Arg Ala Asn Val Ala Val Val Ser Gly Ala Pro
1               5                   10                  15

<210> SEQ ID NO 39
<211> LENGTH: 13
<212> TYPE: PRT
<213> ORGANISM: Homo sapiens

<400> SEQUENCE: 39

Pro Ala Ile Leu Ser Glu Ala Ser Ala Pro Ile Pro His
1               5                   10

<210> SEQ ID NO 40
<211> LENGTH: 14
<212> TYPE: PRT
<213> ORGANISM: Homo sapiens

<400> SEQUENCE: 40

Lys Val Ile Gln Ala Gln Thr Ala Phe Ser Ala Asn Pro Ala
1               5                   10

<210> SEQ ID NO 41
<211> LENGTH: 17
<212> TYPE: PRT
<213> ORGANISM: Homo sapiens

<400> SEQUENCE: 41

Asn Gly Ala Tyr Lys Ala Ile Pro Val Ala Gln Asp Leu Asn Ala Pro
1               5                   10                  15

Ser

<210> SEQ ID NO 42
<211> LENGTH: 16
<212> TYPE: PRT
<213> ORGANISM: Homo sapiens

<400> SEQUENCE: 42

Thr Asn Gly Val Val His Val Ile Thr Asn Val Leu Gln Pro Pro Ala
1               5                   10                  15

<210> SEQ ID NO 43
<211> LENGTH: 16
<212> TYPE: PRT
<213> ORGANISM: Homo sapiens -continued

```
<400> SEQUENCE: 43

Thr Thr Thr Gln Leu Tyr Thr Asp Arg Thr Glu Lys Leu Arg Pro Glu
1               5                   10                  15

<210> SEQ ID NO 44
<211> LENGTH: 15
<212> TYPE: PRT
<213> ORGANISM: Homo sapiens

<400> SEQUENCE: 44

Gly Lys Lys Glu Tyr Leu Ile Ala Gly Lys Ala Glu Gly Asp Gly
1               5                   10                  15

<210> SEQ ID NO 45
<211> LENGTH: 15
<212> TYPE: PRT
<213> ORGANISM: Homo sapiens

<400> SEQUENCE: 45

Met Gly Glu Ile Ala Ser Phe Asp Lys Ala Lys Leu Lys Lys Thr
1               5                   10                  15

<210> SEQ ID NO 46
<211> LENGTH: 14
<212> TYPE: PRT
<213> ORGANISM: Homo sapiens

<400> SEQUENCE: 46

Met Ala Glu Ile Glu Lys Phe Asp Lys Ser Lys Leu Lys Lys
1               5                   10

<210> SEQ ID NO 47
<211> LENGTH: 15
<212> TYPE: PRT
<213> ORGANISM: Homo sapiens

<400> SEQUENCE: 47

Val Val Ser Ser Ile Glu Gln Lys Thr Glu Gly Ala Glu Lys Lys
1               5                   10                  15

<210> SEQ ID NO 48
<211> LENGTH: 13
<212> TYPE: PRT
<213> ORGANISM: Homo sapiens

<400> SEQUENCE: 48

His Ser Lys Ile Ile Ile Ile Lys Lys Gly His Ala Lys
1               5                   10

<210> SEQ ID NO 49
<211> LENGTH: 15
<212> TYPE: PRT
<213> ORGANISM: Homo sapiens

<400> SEQUENCE: 49

Asn Pro Pro Ser Met Val Ala Ala Gly Ser Val Val Ala Ala Val
1               5                   10                  15

<210> SEQ ID NO 50
<211> LENGTH: 20
<212> TYPE: PRT
<213> ORGANISM: Homo sapiens

<400> SEQUENCE: 50
```

```
Trp Ile Ser Lys Gln Glu Tyr Asp Glu Ser Gly Pro Ser Ile Val His
1               5                   10                  15

Arg Lys Cys Phe
            20

<210> SEQ ID NO 51
<211> LENGTH: 13
<212> TYPE: PRT
<213> ORGANISM: Homo sapiens

<400> SEQUENCE: 51

Leu Lys Lys Tyr Leu Tyr Glu Ile Ala Arg Arg His Pro
1               5                   10

<210> SEQ ID NO 52
<211> LENGTH: 13
<212> TYPE: PRT
<213> ORGANISM: Homo sapiens

<400> SEQUENCE: 52

Thr Leu Val Glu Val Ser Arg Asn Leu Gly Lys Val Gly
1               5                   10

<210> SEQ ID NO 53
<211> LENGTH: 16
<212> TYPE: PRT
<213> ORGANISM: Homo sapiens

<400> SEQUENCE: 53

Thr Pro Thr Leu Val Glu Val Ser Arg Asn Leu Gly Lys Val Gly Ser
1               5                   10                  15

<210> SEQ ID NO 54
<211> LENGTH: 21
<212> TYPE: PRT
<213> ORGANISM: Homo sapiens

<400> SEQUENCE: 54

Glu Lys Ser Lys Glu Gln Leu Thr Pro Leu Ile Lys Lys Ala Gly Thr
1               5                   10                  15

Glu Leu Val Asn Phe
            20

<210> SEQ ID NO 55
<211> LENGTH: 16
<212> TYPE: PRT
<213> ORGANISM: Homo sapiens

<400> SEQUENCE: 55

Tyr Pro Lys Ser Leu His Met Tyr Ala Asn Arg Leu Leu Asp His Arg
1               5                   10                  15

<210> SEQ ID NO 56
<211> LENGTH: 14
<212> TYPE: PRT
<213> ORGANISM: Homo sapiens

<400> SEQUENCE: 56

Glu Pro Tyr Tyr Lys Met Gln Thr Arg Ala Gly Ser Arg Glu
1               5                   10

<210> SEQ ID NO 57
<211> LENGTH: 20
```

-continued

```
<212> TYPE: PRT
<213> ORGANISM: Homo sapiens

<400> SEQUENCE: 57

Ala Pro Pro Ser Gly Gly Pro Gly Phe Leu Ser Ile Glu Arg Pro Asp
1               5                   10                  15

Ser Arg Pro Pro
            20

<210> SEQ ID NO 58
<211> LENGTH: 14
<212> TYPE: PRT
<213> ORGANISM: Homo sapiens

<400> SEQUENCE: 58

Phe Gly Pro Ile Tyr Asn Tyr Lys Asp Thr Ile Val Phe Lys
1               5                   10

<210> SEQ ID NO 59
<211> LENGTH: 12
<212> TYPE: PRT
<213> ORGANISM: Homo sapiens

<400> SEQUENCE: 59

Ser Pro Asp Pro Ser Ile Tyr Ala Tyr Asp Asn Phe
1               5                   10

<210> SEQ ID NO 60
<211> LENGTH: 23
<212> TYPE: PRT
<213> ORGANISM: Homo sapiens

<400> SEQUENCE: 60

Glu Pro Pro Val Ile Gln Asn Pro Glu Tyr Lys Gly Glu Trp Lys Pro
1               5                   10                  15

Arg Gln Ile Asp Asn Pro Asp
            20

<210> SEQ ID NO 61
<211> LENGTH: 13
<212> TYPE: PRT
<213> ORGANISM: Homo sapiens

<400> SEQUENCE: 61

Gly Val Ile Lys Val Phe Asn Asp Met Lys Val Arg Lys
1               5                   10

<210> SEQ ID NO 62
<211> LENGTH: 15
<212> TYPE: PRT
<213> ORGANISM: Homo sapiens

<400> SEQUENCE: 62

Ala Pro Gly Tyr Leu Ala Ile Thr Lys Lys Val Ala Val Pro Tyr
1               5                   10                  15

<210> SEQ ID NO 63
<211> LENGTH: 16
<212> TYPE: PRT
<213> ORGANISM: Homo sapiens

<400> SEQUENCE: 63

Ala Ser Val Asp Leu Lys Asn Thr Gly Arg Glu Glu Phe Leu Thr Ala
1               5                   10                  15
```

<210> SEQ ID NO 64
<211> LENGTH: 16
<212> TYPE: PRT
<213> ORGANISM: Homo sapiens

<400> SEQUENCE: 64

Gly Asn His Gln Phe Ala Lys Tyr Lys Ser Phe Lys Val Ala Asp Glu
1               5                   10                  15

<210> SEQ ID NO 65
<211> LENGTH: 15
<212> TYPE: PRT
<213> ORGANISM: Homo sapiens

<400> SEQUENCE: 65

Val Ser His Phe Phe Arg Glu Leu Ala Glu Glu Lys Arg Glu Gly
1               5                   10                  15

<210> SEQ ID NO 66
<211> LENGTH: 14
<212> TYPE: PRT
<213> ORGANISM: Homo sapiens

<400> SEQUENCE: 66

Thr Pro Asp Ala Met Lys Ala Ala Met Ala Leu Glu Lys Lys
1               5                   10

<210> SEQ ID NO 67
<211> LENGTH: 12
<212> TYPE: PRT
<213> ORGANISM: Homo sapiens

<400> SEQUENCE: 67

Phe Val Met Gly Val Asn His Glu Lys Tyr Asp Asn
1               5                   10

<210> SEQ ID NO 68
<211> LENGTH: 13
<212> TYPE: PRT
<213> ORGANISM: Homo sapiens

<400> SEQUENCE: 68

Thr Gly Val Phe Thr Thr Met Glu Lys Ala Gly Ala His
1               5                   10

<210> SEQ ID NO 69
<211> LENGTH: 25
<212> TYPE: PRT
<213> ORGANISM: Homo sapiens

<400> SEQUENCE: 69

Ile Ser Trp Tyr Asp Asn Glu Phe Gly Tyr Ser Asn Arg Val Val Asp
1               5                   10                  15

Leu Met Ala His Met Ala Ser Lys Glu
            20                  25

<210> SEQ ID NO 70
<211> LENGTH: 22
<212> TYPE: PRT
<213> ORGANISM: Homo sapiens

<400> SEQUENCE: 70

Gly Thr Gly Ala Ser Gly Ser Phe Lys Leu Asn Lys Lys Ala Ala Ser

```
              1               5                  10                  15

Gly Glu Ala Lys Pro Lys
                    20

<210> SEQ ID NO 71
<211> LENGTH: 15
<212> TYPE: PRT
<213> ORGANISM: Homo sapiens

<400> SEQUENCE: 71

Asp Val Gly Val Tyr Arg Ala Val Thr Pro Gln Gly Arg Pro Asp
1               5                  10                  15

<210> SEQ ID NO 72
<211> LENGTH: 15
<212> TYPE: PRT
<213> ORGANISM: Homo sapiens

<400> SEQUENCE: 72

Asp Val Gly Glu Phe Arg Ala Val Thr Glu Leu Gly Arg Pro Asp
1               5                  10                  15

<210> SEQ ID NO 73
<211> LENGTH: 16
<212> TYPE: PRT
<213> ORGANISM: Homo sapiens

<400> SEQUENCE: 73

His Pro Leu His Ser Lys Ile Ile Ile Lys Lys Gly His Ala Lys
1               5                  10                  15

<210> SEQ ID NO 74
<211> LENGTH: 14
<212> TYPE: PRT
<213> ORGANISM: Homo sapiens

<400> SEQUENCE: 74

Asp Lys Asp Leu Phe Lys Ala Val Asp Ala Ala Leu Lys Lys
1               5                  10

<210> SEQ ID NO 75
<211> LENGTH: 14
<212> TYPE: PRT
<213> ORGANISM: Homo sapiens

<400> SEQUENCE: 75

Lys Asp Lys Thr Tyr Ser Tyr Leu Asn Lys Leu Pro Val Lys
1               5                  10

<210> SEQ ID NO 76
<211> LENGTH: 19
<212> TYPE: PRT
<213> ORGANISM: Homo sapiens

<400> SEQUENCE: 76

Val Ile Lys Met Gly Val Ala Ala His Lys Lys Ser His Glu Glu Ser
1               5                  10                  15

His Lys Glu

<210> SEQ ID NO 77
<211> LENGTH: 21
<212> TYPE: PRT
<213> ORGANISM: Homo sapiens
```

```
<400> SEQUENCE: 77

Met Ile Glu Gln Asn Thr Lys Ser Pro Leu Phe Met Gly Lys Val Val
1               5                   10                  15

Asn Pro Thr Gln Lys
            20

<210> SEQ ID NO 78
<211> LENGTH: 15
<212> TYPE: PRT
<213> ORGANISM: Homo sapiens

<400> SEQUENCE: 78

Gly Pro His Phe Asn Pro Leu Ser Arg Lys His Gly Gly Pro Lys
1               5                   10                  15

<210> SEQ ID NO 79
<211> LENGTH: 16
<212> TYPE: PRT
<213> ORGANISM: Homo sapiens

<400> SEQUENCE: 79

Asp Pro Gln Thr Phe Tyr Tyr Ala Val Ala Val Val Lys Lys Asp Ser
1               5                   10                  15
```